US011534444B2

(12) United States Patent
Pfefen et al.

(10) Patent No.: US 11,534,444 B2
(45) Date of Patent: Dec. 27, 2022

(54) TREATMENT OF SMA

(71) Applicant: Hoffmann-La Roche Inc., Little Falls, NJ (US)

(72) Inventors: Jean-Paul Pfefen, Basel (CH); Heidemarie Kletzl, Basel (CH); Lutz Mueller, Basel (CH)

(73) Assignee: Hoffmann-La Roche Inc., Little Falls, NJ (US)

(*) Notice: Subject to any disclaimer, the term of this patent is extended or adjusted under 35 U.S.C. 154(b) by 3 days.

(21) Appl. No.: 16/838,942

(22) Filed: Apr. 2, 2020

(65) Prior Publication Data

US 2020/0375993 A1 Dec. 3, 2020

Related U.S. Application Data

(63) Continuation of application No. PCT/EP2018/076577, filed on Oct. 1, 2018.

(30) Foreign Application Priority Data

Oct. 3, 2017 (EP) .................................... 17194520

(51) Int. Cl.
*A61K 31/519* (2006.01)
*A61P 21/00* (2006.01)
*A61K 9/00* (2006.01)

(52) U.S. Cl.
CPC .......... *A61K 31/519* (2013.01); *A61K 9/0053* (2013.01); *A61P 21/00* (2018.01)

(58) Field of Classification Search
CPC .................................................... A61K 31/519
See application file for complete search history.

(56) References Cited

U.S. PATENT DOCUMENTS

| 9,969,754 B2 * | 5/2018 | Ratni ................... C07D 487/04 |
| 2017/0197990 A1 * | 7/2017 | Ratni ..................... A61P 25/28 |

FOREIGN PATENT DOCUMENTS

| EP | 3143025 A1 | 3/2017 |
| WO | 2015/173181 A1 | 11/2015 |
| WO | WO2015173181 | * 11/2015 |
| WO | 2017/081111 A1 | 5/2017 |
| WO | 2017080967 A1 | 5/2017 |

OTHER PUBLICATIONS

Arnold, W., et al., "Spinal Muscular Atrophy: Diagnosis and Management in a New Therapeutic Era" Muscle Nerve 51(2):157-167 (Feb. 1, 2015).
CAS Registry Database, 1825352-65-5, (Risdiplam [USAN:INN]), pp. 1 Other Date Jun 18, 2020 https://chem.nlm.nih.gov/chemidplus/rn/1825352-65-5.
Clinical Trials.gov et al., "A Study to Investigate the Safety, Tolerability, Pharmacokinetics, Pharmacodynamics and Efficacy of Risdiplam (RO7034067) in Type 2 and 3 Spinal Muscular Atrophy (SMA) Participants (SUNFISH)" (NCT02908685—Drug: Risdiplam; Other Name: RO7034067; Other Study ID: BP39055; First Posted: Sep. 21, 2016; Last Update Posted: Mar. 24, 2020; Printed: Jun. 16, 2020),:1-9 https://clinicaltrials.gov/ct2/show/NCT02908685.
Griffin, W., et al., "Classification of Surface—Active Agents by 'HLB'" J Soc Cosmet Chem 1:311-326 ( 1949).
"International Preliminary Report on Patentability—PCT/EP2018/076577" (dated Apr. 8, 2020),:pp. 1-9 (Apr. 16, 2020).
"International Search Report—PCT/EP2018/076577":pp. 1-16 (dated Jan. 23, 2019).
Lewelt, A., et al., "New Therapeutic Approaches to Spinal Muscular Atrophy" Curr Neurol Neurosci Rep 12(1):42-53 (Feb. 1, 2012).
Livak, K., et al., "Analysis of Relative Gene Expression Data Using Real-Time Quantitative PCR and the 2-ΔΔCT Method" Methods 25(4):402-408 (Dec. 1, 2001).
Metfalfe, S., et al, "Rapamycin and p53 act on different pathways to induce G1 arrest in mammalian cells" Oncogene 15(14):1635-1642 (Oct. 2, 1997).
Palacino, J., et al., "SMN2 splice modulators enhance U1-pre-mRNA association and rescue SMA mice" Nat Chem Biol 11:511-517 (Jun. 1, 2015).
Ver Hoeve, J., et al., "Gender Differences in Anesthetized Primate ERG and Full-field Flash VEP" IOVS (ARVO Annual Meeting Abstract), 55(13):5130 (Apr. 1, 2014).
Zhao, X., et al., "Pharmacokinetics, pharmacodynamics, and efficacy of a small-molecule SMN2 splicing modifier in mouse models of spinal muscular atrophy" Hum Mol Genet 25(10):1885-1899 (Feb. 29, 2016).

* cited by examiner

*Primary Examiner* — Rei Tsang Shiao
(74) *Attorney, Agent, or Firm* — Bradley E. Davis

(57) ABSTRACT

The present invention relates to 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of spinal muscular atrophy (SMA), its pharmaceutical composition to be used in the treatment of SMA, its methods of treatment thereof.

35 Claims, 10 Drawing Sheets

Specification includes a Sequence Listing.

SEQUENCE LISTING

<160> NUMBER OF SEQ ID NOS: 9

<210> SEQ ID NO 1
<211> LENGTH: 17
<212> TYPE: DNA
<213> ORGANISM: Homo sapiens

<400> SEQUENCE: 1
cccccaaggt gctgcta                                                  17

<210> SEQ ID NO 2
<211> LENGTH: 21
<212> TYPE: DNA
<213> ORGANISM: Homo sapiens

<400> SEQUENCE: 2
tgaactggaa gcaaaggaga a                                             21

<210> SEQ ID NO 3
<211> LENGTH: 20
<212> TYPE: DNA
<213> ORGANISM: Homo sapiens

<400> SEQUENCE: 3
ctttcttctg caggaccagg                                               20

<210> SEQ ID NO 4
<211> LENGTH: 20
<212> TYPE: DNA
<213> ORGANISM: Homo sapiens

<400> SEQUENCE: 4
gaaggtgaag gtcggagtca                                               20

<210> SEQ ID NO 5
<211> LENGTH: 24
<212> TYPE: DNA
<213> ORGANISM: Homo sapiens

<400> SEQUENCE: 5
aaccatgtag ttgaggtcaa tgaa                                          24

<210> SEQ ID NO 6
<211> LENGTH: 8
<212> TYPE: DNA
<213> ORGANISM: Homo sapiens

<400> SEQUENCE: 6 ttgatggc                                                             8

```
<210> SEQ ID NO 7
<211> LENGTH: 17
<212> TYPE: DNA
<213> ORGANISM: Homo sapiens

<400> SEQUENCE: 7
cccccaaggt gctgcta                                                  17

<210> SEQ ID NO 8
<211> LENGTH: 21
<212> TYPE: DNA
<213> ORGANISM: Homo sapiens

<400> SEQUENCE: 8
tgaactggaa gcaaaggaca c                                             21

<210> SEQ ID NO 9
<211> LENGTH: 20
<212> TYPE: DNA
<213> ORGANISM: Homo sapiens

<400> SEQUENCE: 9
cttccttctg cagggccagg                                               20
```

TREATMENT OF SMA

CROSS REFERENCE TO RELATED APPLICATIONS

This application is a continuation of International Application No. PCT/EP2018/076577, filed Oct. 1, 2018, which claims benefit to European Patent Application No. 17194520.7, filed Oct. 3, 2017; all of which are incorporated by reference in their entirety.

SEQUENCE LISTING

This application contains a Sequence Listing which has been submitted via EFS-Web and is hereby incorporated by reference in its entirety. Said ASCII copy, created on Mar. 23, 2020, is named P34471-US_Sequence_Listing.txt and is 1,577 bytes in size.

FIELD OF THE INVENTION

The invention relates to 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of spinal muscular atrophy (SMA), its pharmaceutical composition to be used in the treatment of SMA, its methods of treatment thereof.

Spinal muscular atrophy (SMA), in its broadest sense, describes a collection of inherited and acquired central nervous system (CNS) diseases characterized by progressive motor neuron loss in the spinal cord and brainstem causing muscle weakness and muscle atrophy. SMA is characterized by a degeneration of the alpha motor neurons from the anterior horn of the spinal cord leading to muscular atrophy and resulting in paralysis. This alpha motor neuron degeneration thus substantially compromises the vital prognosis of patients. In healthy subjects, these neurons transmit messages from the brain to the muscles, leading to the contraction of the latter. In the absence of such a stimulation, the muscles atrophy. Subsequently, in addition to a generalized weakness and atrophy of the muscles, and more particularly of those of the trunk, upper arms and thighs, these disorders can be accompanied by serious respiratory problems.

Infantile SMA is the most severe form of this neurodegenerative disorder. Symptoms include muscle weakness, poor muscle tone, weak cry, limpness or a tendency to flop, difficulty sucking or swallowing, accumulation of secretions in the lungs or throat, feeding difficulties, and increased susceptibility to respiratory tract infections. The legs tend to be weaker than the arms and developmental milestones, such as lifting the head or sitting up, cannot be reached. In general, the earlier the symptoms appear, the shorter the lifespan. As the motor neuron cells deteriorate, symptoms appear shortly afterward. The severe forms of the disease are fatal and all forms have no known cure. The course of SMA is directly related to the rate of motor neuron cell deterioration and the resulting severity of weakness. Infants with a severe form of SMA frequently succumb to respiratory disease due to weakness in the muscles that support breathing. Children with milder forms of SMA live much longer, although they may need extensive medical support, especially those at the more severe end of the spectrum. The clinical spectrum of SMA disorders has been divided into the following five groups:

1) Type 0 SMA (In Utero SMA) is the most severe form of the disease and begins before birth. Usually, the first symptom of Type 0 SMA is reduced movement of the fetus that can first be observed between 30 and 36 weeks of pregnancy. After birth, these newborns have little movement and have difficulties with swallowing and breathing.
2) Type I SMA (Infantile SMA or Werdnig-Hoffmann disease) presents symptoms between 0 and 6 months; this form of SMA is very severe. Patients never achieve the ability to sit, and death usually occurs within the first 2 years without ventilatory support.
3) Type II SMA (Intermediate SMA) has an age of onset at 7-18 months. Patients achieve the ability to sit unsupported, but never stand or walk unaided. Prognosis in this group is largely dependent on the degree of respiratory involvement.
4) Type III SMA (Juvenile SMA or Kugelberg-Welander disease) is generally diagnosed after 18 months. Type 3 SMA individuals are able to walk independently at some point during their disease course but often become wheelchair-bound during youth or adulthood.
5) Type IV SMA (Adult onset SMA). Weakness usually begins in late adolescence in the tongue, hands, or feet, then progresses to other areas of the body. The course of adult SMA is much slower and has little or no impact on life expectancy.

All the forms of spinal muscular atrophy are accompanied by progressive muscle weakness and atrophy subsequent to the degeneration of the neurons from the anterior horn of the spinal cord. SMA currently constitutes one of the most common causes of infant mortality. It equally affects girls or boys in all regions of the world with a prevalence of between 1/6000 and 1/10 000.

There is currently no approved oral treatment for SMA that provides stabilization or improvement of motor function. Several drug candidates are currently under investigation in the nonclinical and clinical settings (Lewelt A, et al, Curr Neurol Neurosci Rep. 2012; 12:42-532; Arnold et al., Muscle Nerve. 2015; 51:157-67) and recently, nusinersen, an intrathecally-administered antisense oligonucleotide which promotes the inclusion of exon 7 in SMN2 pre mRNA, has received approvals in the US, EU and other jurisdictions.

Despite a better understanding of the genetic basis and pathophysiology of SMA, and the several strategies for treatment having been explored, none have yet demonstrated success as an oral treatment in the clinic with limited side effects. The present invention intend to respond to this oral treatment need. 7-(4,7-diazaspiro[2.5]octan-7-yl)-2-(2,8-dimethylimidazo[1,2-b]pyridazin-6-yl)pyrido[1,2-a]pyrimidin-4-one is currently investigated in clinical phase II.

A randomized double blind, placebo-controlled, phase II study on 7-(4,7-diazaspiro[2.5]octan-7-yl)-2-(2,8-dimethylimidazo[1,2-b]pyridazin-6-yl)pyrido[1,2-a]pyrimidin-4-one (NTC02908685 or BP39055) is being performed on SMA type II and type III patients aged 2 to 25 years.

It was found that surprisingly the FMO3 participates on the elimination path way of 7-(4,7-diazaspiro[2.5]octan-7-yl)-2-(2,8-dimethylimidazo[1,2-b]pyridazin-6-yl)pyrido[1,2-a]pyrimidin-4-one, potential having an effect on the dosage of the drug.

In Part 1 of Study BP39055, it was surprisingly found that a median SMN protein increase of 151% (range 49%-251%) versus baseline was observed for the highest evaluated dose of 5 mg in SMA patients 12-25 years old, and a 96% (range 17%-150%) increase in SMN protein was noted for the highest tested dose of 0.25 mg/kg in the 2-11 year age group.

Consequently, it was surprisingly found that the optimum dose would be 0.25 mg/kg once a day for patients with a body weight of less than 20 kg and 5 mg for patients with a body weight of more than or equal to 20 kg. Therefore it is anticipated that the predicted mean exposure (AUC0-24h,ss) for the selected BP39055 Part 2 dose is 1690 ng·h/mL [95% CI 1600-1780 ng·h/mL] for all patients 2 25 years of age.

Based on a monkey study it was surprisingly found that even though one may expect SMN may be increased further, the dose should not be exceeding the exposure with an AUC0-24 h of 1870/2060 ng·h/mL in males and females, respectively to avoid any retina degenerations.

Furthermore an upper dosage limit was also surprisingly found linked to the splicing of FOX M1 and MADD by 7-(4,7-diazaspiro[2.5]octan-7-yl)-2-(2,8-dimethylimidazo[1,2-b]pyridazin-6-yl)pyrido[1,2-a]pyrimidin-4-one. The upper limit dosage is identical than the one linked to retina degeneration.

HET=heterozygous.

Figure 1A:
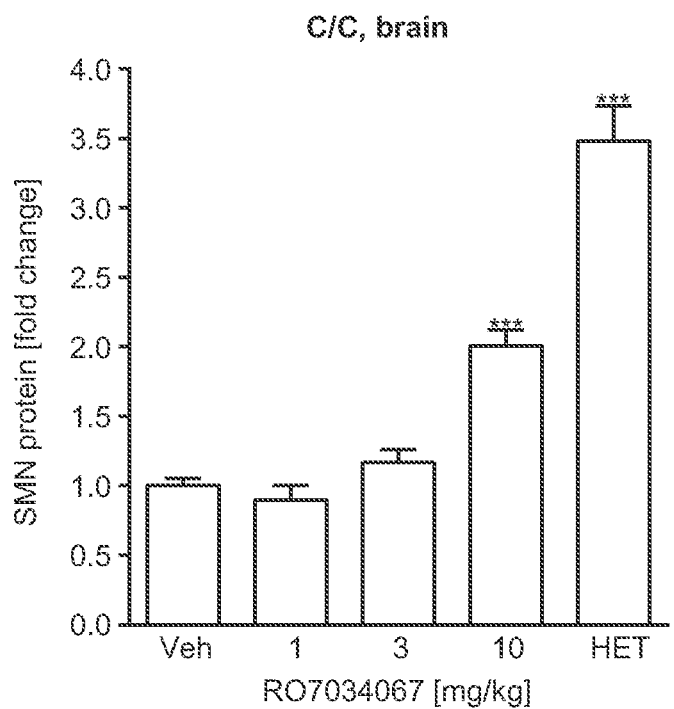
FIG. 1A-FIG. 1D: Increase in SMN Protein Expression In Vivo
Figure 1B:
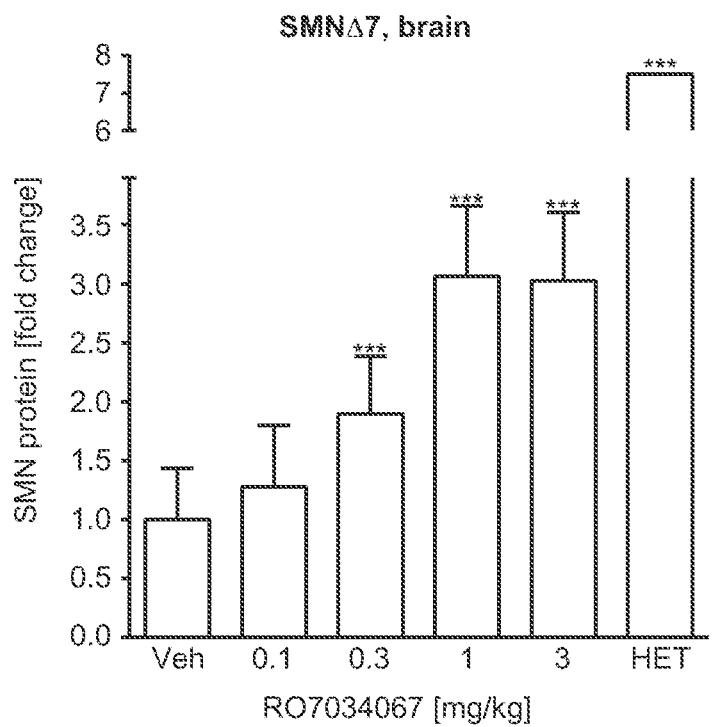
Figure 1C:
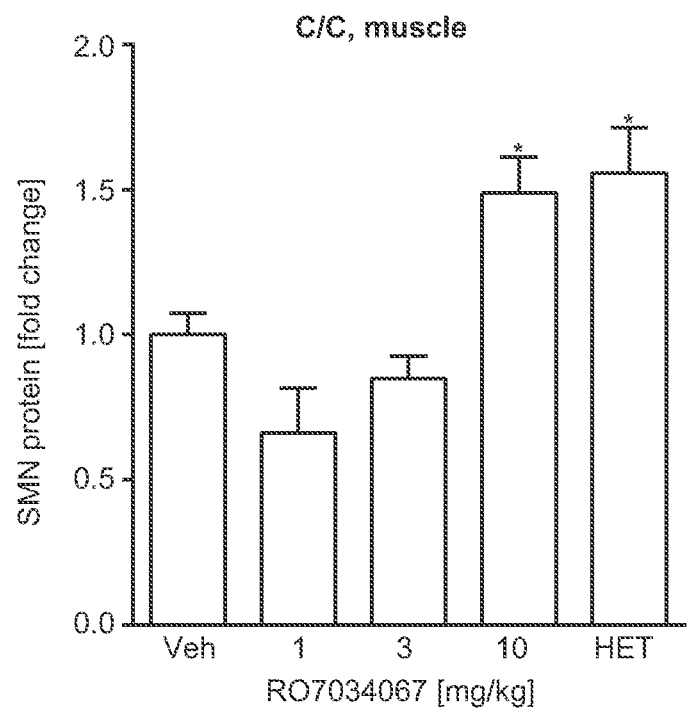
Figure 1D:
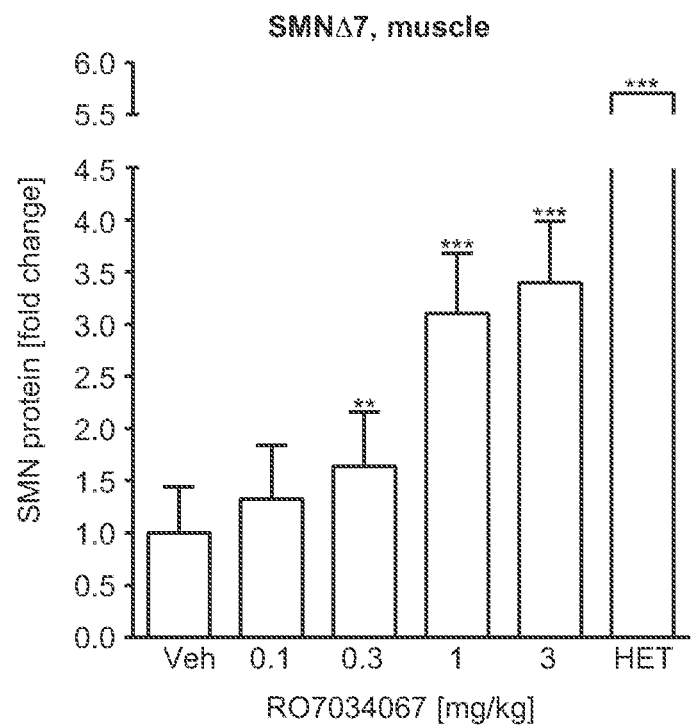

C/C-allele mice and SMNΔ7 mice were treated with RO7034067. One hour after the last dose, brains and quadriceps muscles were collected and levels of SMN protein were assessed by HTRF. FIG. 1A. SMN protein in brains of C/C-allele mice. FIG. 1B. SMN protein in brains of SMNΔ7 mice. FIG. 1C. SMN protein in quadriceps muscle of C/C-allele mice. FIG. 1D. SMN protein in quadriceps muscle of SMNΔ7 mice. Data represent means±SEM of 5-6 animals per group and are expressed as fold change vs. vehicle-treated controls. *=p<0.05, =p<0.01, *=p<0.001 vs. untreated controls.

Figure 2A:
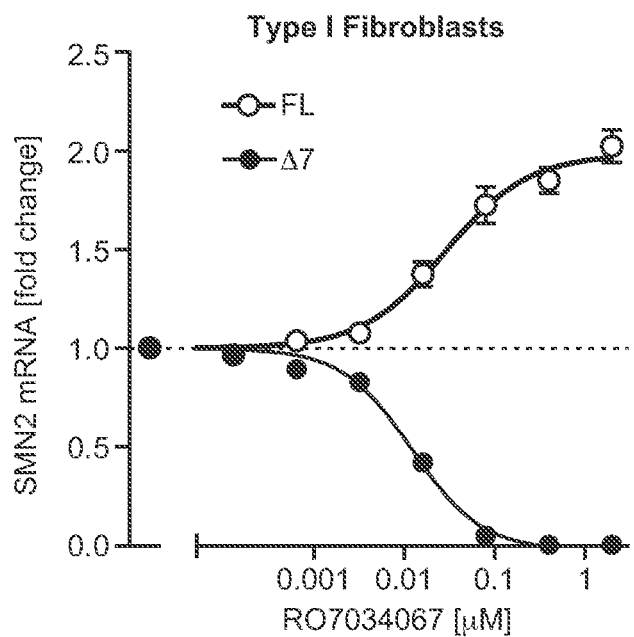
Figure 2B:
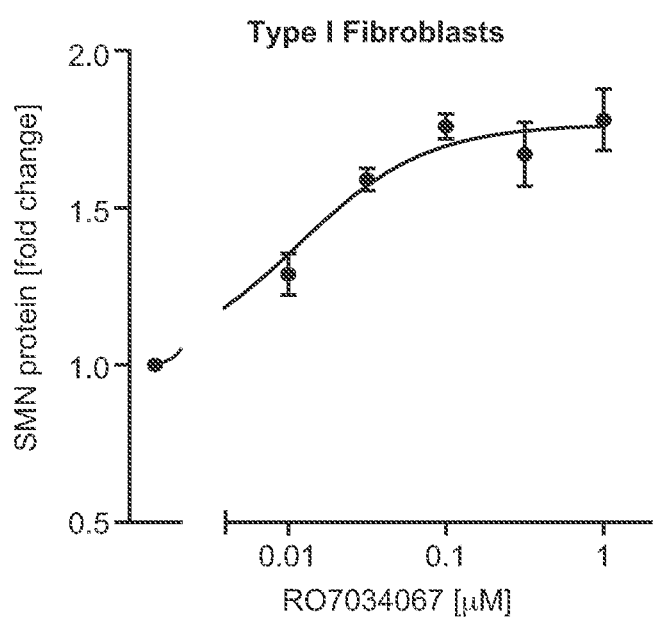
Figure 2C:
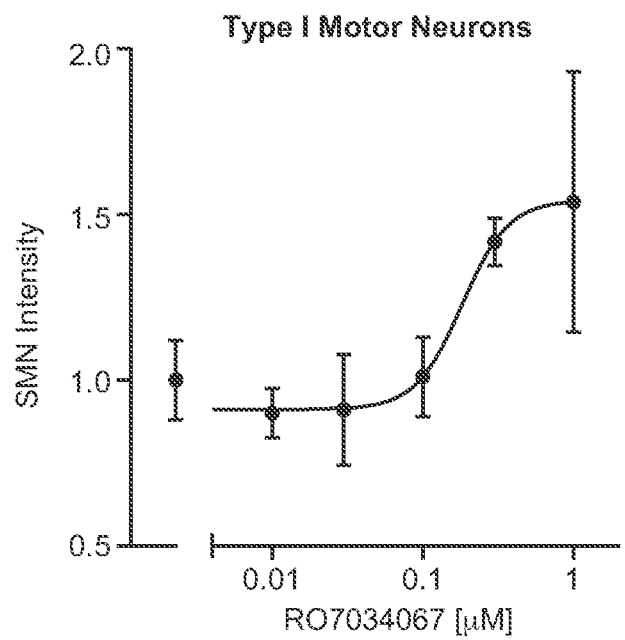
Figure 2D:
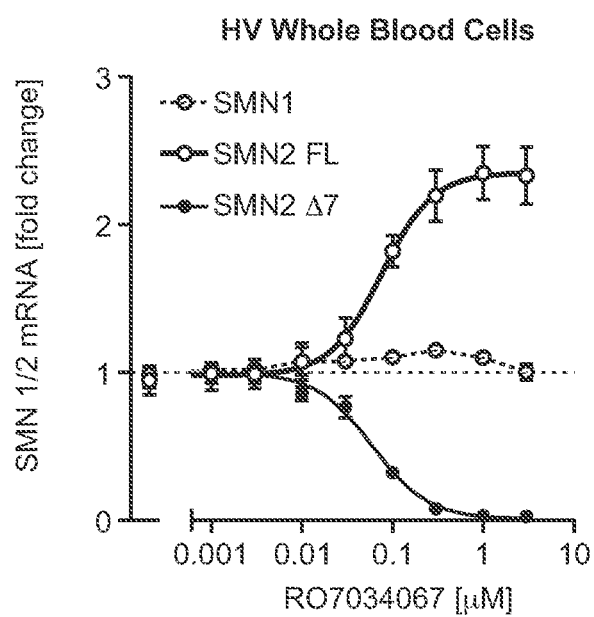

FIG. 2A-FIG. 2D: RO7034067 Increases SMN mRNA and Protein Production In Vitro;

Fibroblasts from SMA Type 1 patients were cultured for 24 hours (A) or 48 hours (B); motor neurons from SMA Type 1 patient iPSCs were cultured for 72 hours (C) and whole blood cells from healthy volunteers (HV) for 4 hours (D) in the presence or absence of RO7034067. SMN splicing was assessed by reverse transcription polymerase chain reaction (RT-PCR), and SMN protein levels were assessed by homogenous time-resolved fluorescence (HTRF) in fibroblast lysates, and by immunostaining for SMN in motor neurons. FIG. 2A. SMN2 splicing in SMA Type 1 fibroblasts. FIG. 2B. SMN protein in SMA Type 1 fibroblasts. FIG. 2C. SMN protein in SMA Type 1 motor neurons. FIG. 2D. SMN1 and SMN2 splicing in whole blood derived from HV. Data represent means±SEM of 3 evaluations per data point and are expressed as fold change vs. untreated controls.

Figure 3:
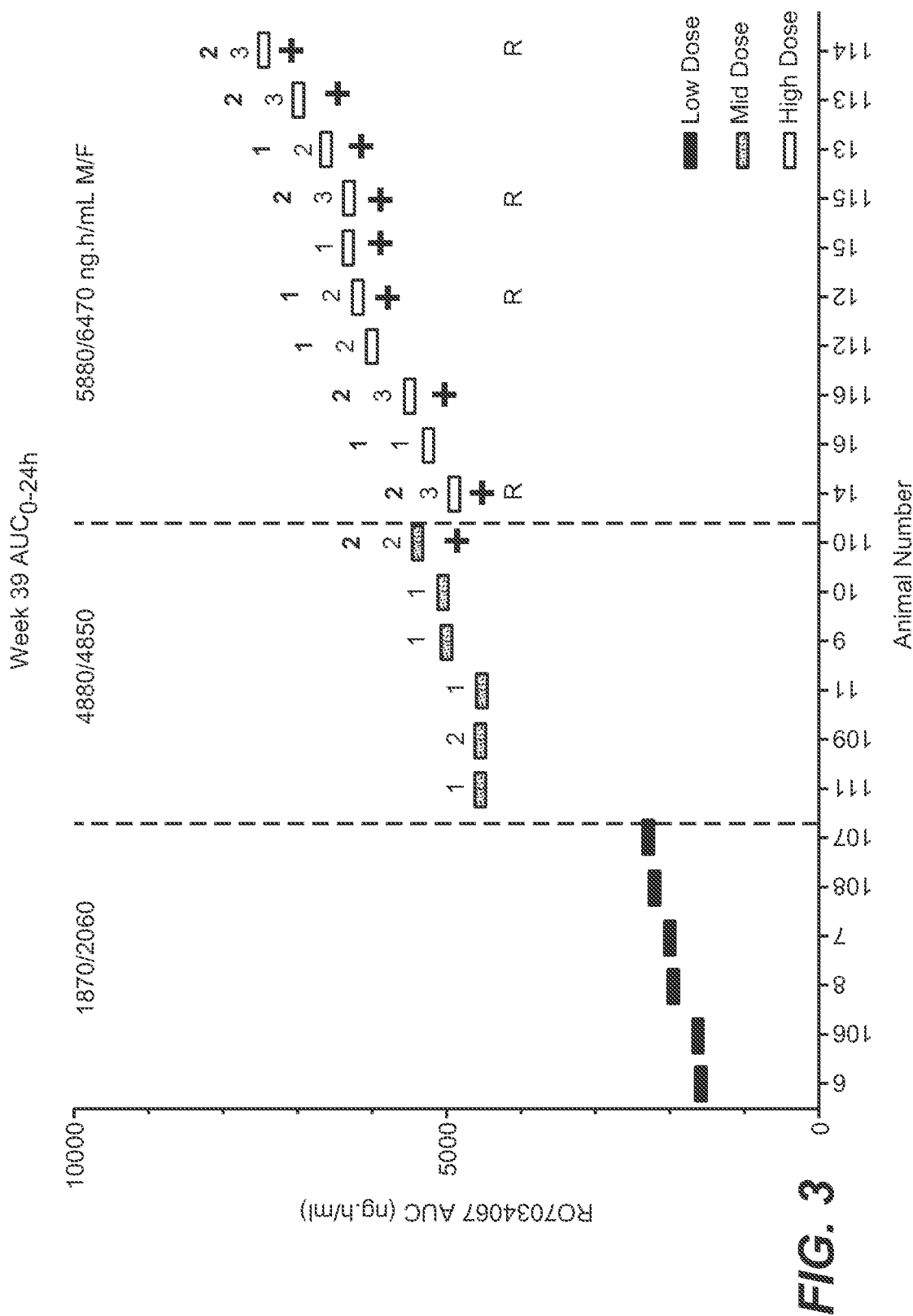

FIG. 3: Association between Effects Recorded in the Retina by sdOCT, ERG and Histopathology with Exposure in Individual Monkeys over the 39-week Study Duration and in 22 weeks of Recovery (for Histopathology).

Individual animal exposures (AUC0-24 h) at study end plotted against retina effects as detected by sdOCT and ERG in the monkey with chronic treatment of R7034067. The worst sdOCT/ERG grading at any of the three time-points was taken. Numbers on the X-axis refer to individual animal numbers in the study. + Symbols indicate presence of retina findings in histology. R: denotes animals still in the recovery phase. Numbers 1, 2, 3 in the graph refer to severity grading of retina effects by sdOCT at the end of the treatment phase as follows:

1. Mild: Retinal changes (disorganization/thinning of layers) only seen in periphery; layers may be thinned/disorganized but not absent; increased or decreased reflectivity, haziness may be seen in retinal layers; hyper-reflective spots (HRS) may be seen in inner retinal layers and inner segment/outer segment junction (IS/OS).
2. Moderate: Retinal changes (disorganization/thinning) seen closer to the macula; layers (e.g., IS/OS) may be discontinuous or absent; MMD may be present but confined to small area temporal to the optic nerve head; mottled periphery in FAF images; HRS may be seen in RPE where IS/OS is absent).
3. Marked: MMD more widespread e.g., on either side of the macula; disruptions, optically empty spaces under the inner limiting membrane and in the outer nuclear layer.

Bolded numbers 1 and 2 in the graph refer to retina effects by ERG. Based on a historical sample of >300 animals, a grading of '1' is assigned to B-wave amplitudes lower than 1.96 standard deviations (SDs) below the expected mean but higher than or equal to 2.36*SDs, and a grading of '2' assigned to B-wave amplitudes below 2.36 SDs from the expected mean. Animals with consistently depressed B-wave amplitude were included with their grading at the end of the treatment phase. Control and treated animals with occasional low B-waves were excluded.

Figure 4:
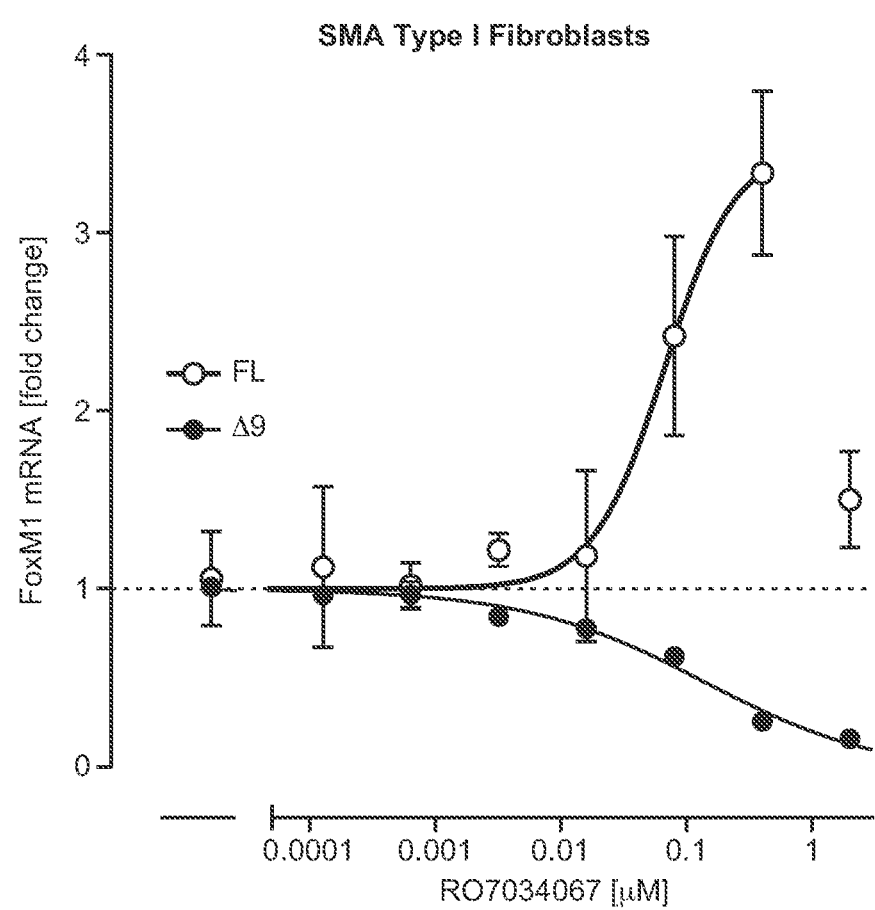

FIG. 4: Alternative Splicing of FoxM1 In Vitro

SMA Type 1 patient fibroblasts were treated with RO7034067 for 24 hours, and FoxM1 full-length (FL) and exon 9-lacking (Δ9) mRNAs were analyzed by RT-qPCR. Data represent means±SEM of 6 repetitions and are expressed as fold change vs. untreated controls.

Figure 5A:
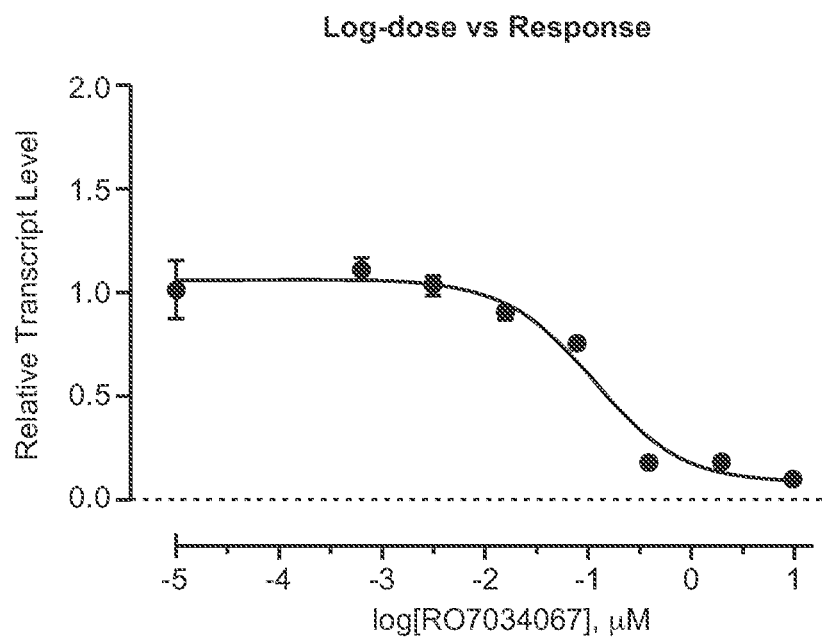
Figure 5B:
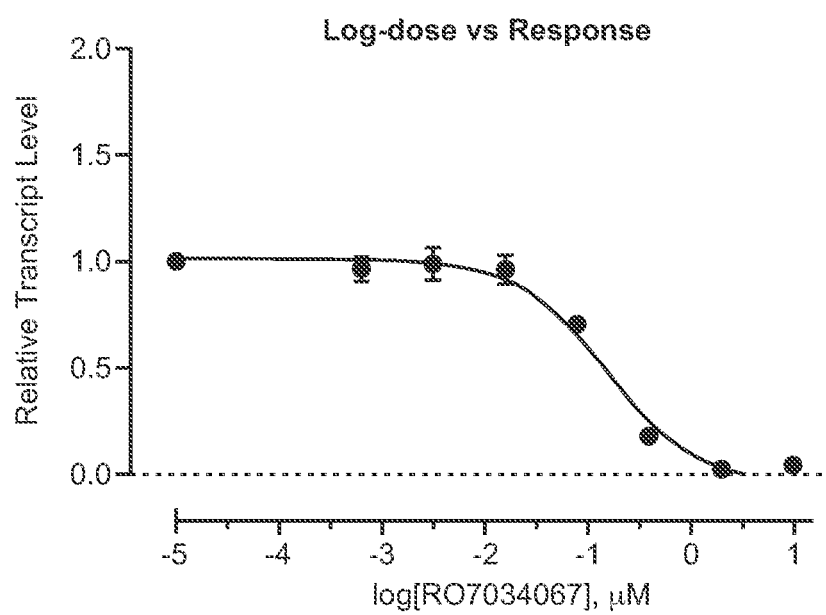
Figure 6:
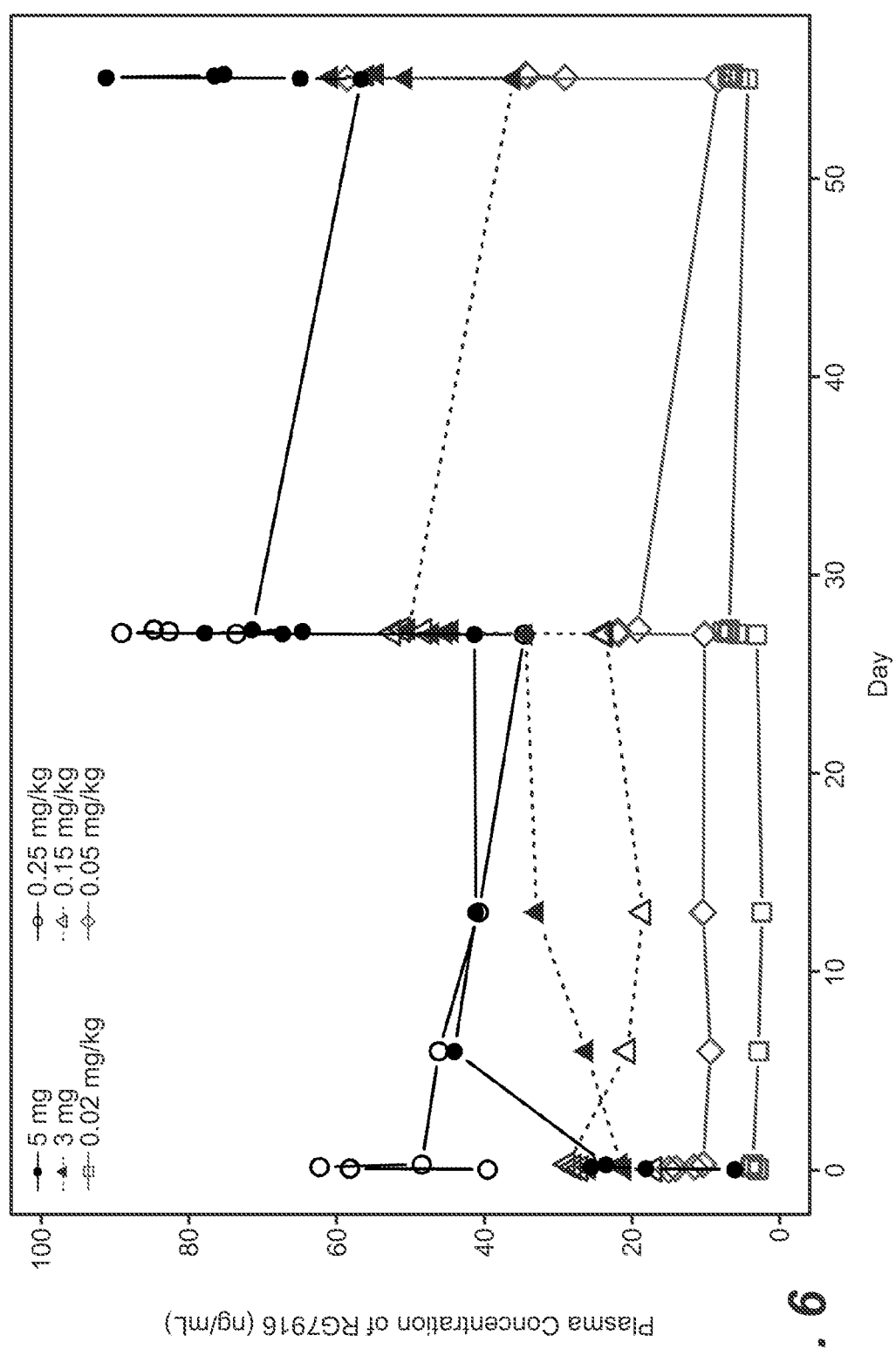

FIG. 5A-FIG. 5B: Effect of RO7034067 on FOXM1 mRNA expression levels in human and Cynomolgus monkey iPSCs Cells were treated with RO7034067 for 24 hours, and FOXM1 B/C transcript variants were analyzed by RT-PCR. Data represent means SEM of 3 repetitions and are expressed as fold change vs. controls. IC50 values are indicated. FIG. 5A. human iPSCs. FIG. 5B. Cynomolgus monkey iPSCs FIG. 6: Plasma concentrations of RG7916. Plasma concentration of RG7916 versus time is plotted by dose.

Figure 7:
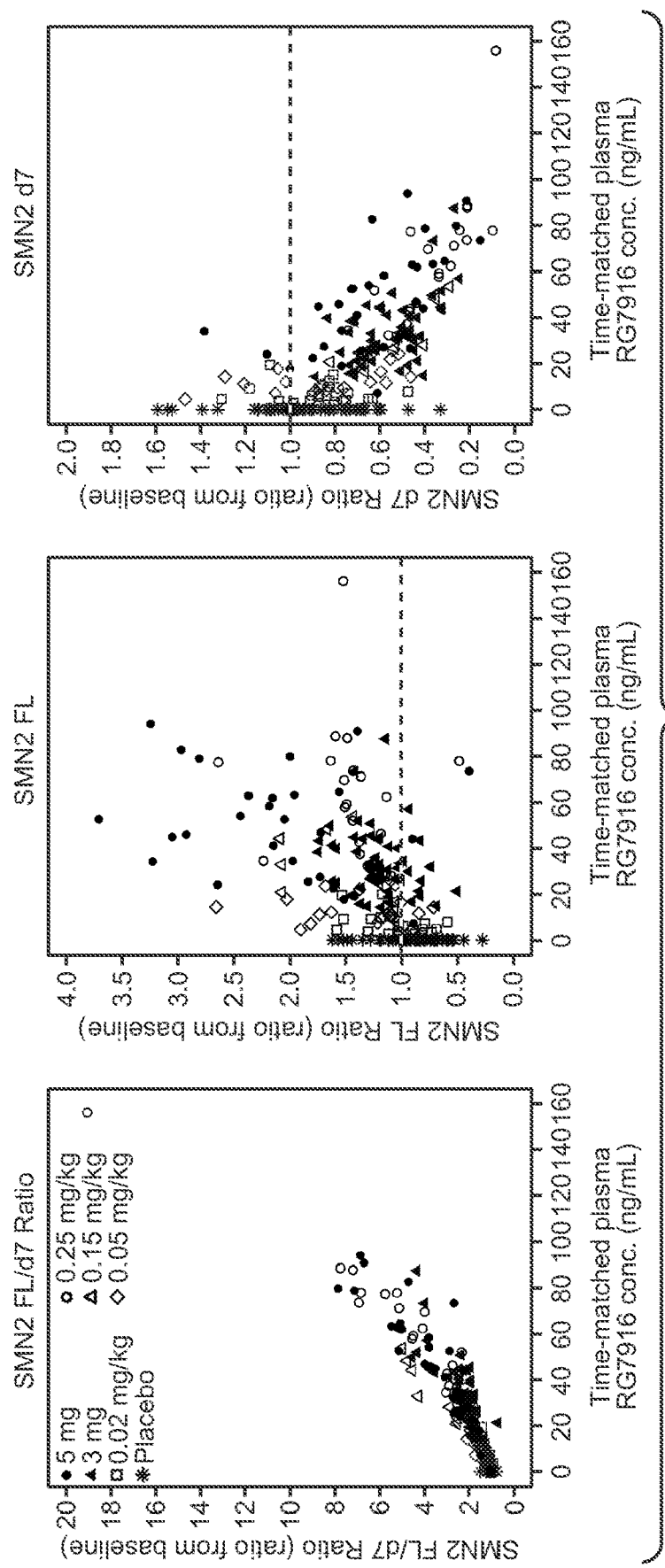
Figure 8:
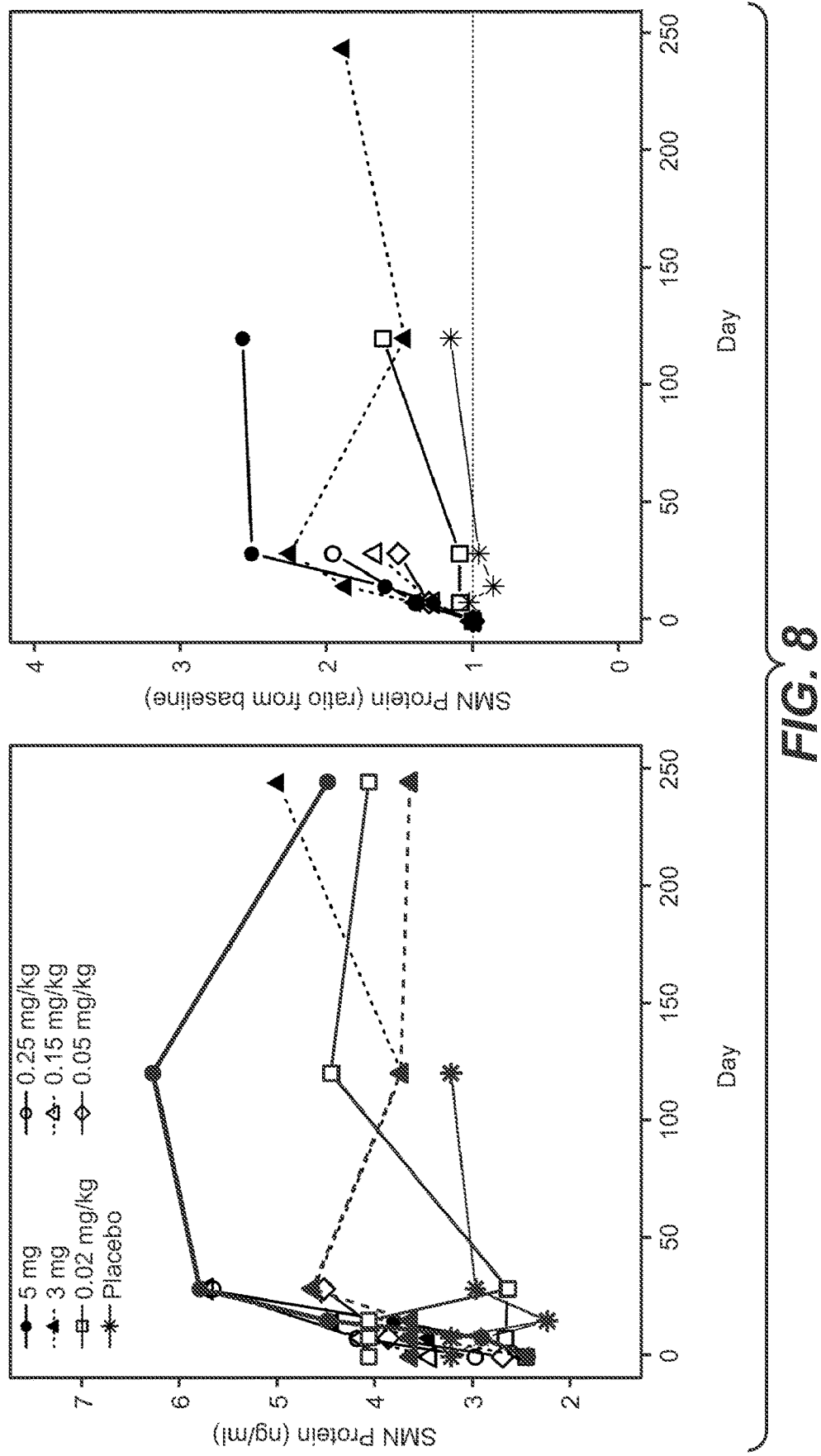

FIG. 7: Plasma concentrations of RG7916 versus SMN2 mRNA levels. Time-matched concentration of RG7916 versus (A) the ratio of SMN2 full-length mRNA to SMNΔ7 mRNA, (B) SMN2 full-length mRNA, or (C) SMNΔ7 mRNA is plotted FIG. 8: SMN protein levels. (A) Concentration of SMN protein in blood by dose. Ratio of SMN protein change from baseline in blood is plotted by dose in (B)

All publications, patent applications, patents and other references mentioned herein are incorporated by reference in their entirety.

The nomenclature used in the present application is based on IUPAC systematic nomenclature, unless indicated otherwise.

Various features and embodiments of the present invention are disclosed herein, however other features of the invention, modifications and equivalents will be apparent to a person skilled in the relevant art, based on the teachings provided. The invention described is not limited to the examples and embodiments provided, various alternatives equivalents will be appreciate by those skilled in the art. As used herein, the singular forms "a", "an" and "the" include the plural unless the context clearly dictates otherwise. For example, "a" individual will also include "individuals".

Unless otherwise stated, the following terms used in the specification and claims have the meanings given below:

The term "FMO3" refers to Flavin-containing monooxygenase 3, also known as dimethylaniline monooxygenase [N-oxide-forming] 3 and trimethylamine monooxygenase, with its enzyme commission number (EC number) EC 1.14.13.148, MGI reference 1100496, Cytogenetic location: 1q24.3 and Genomic coordinates (GRCh38): 1:171,090, 872-171,117,818

An "individual" or "subject", used interchangeably, is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human. In a particular embodiment of the invention the subject is a human with spinal muscular atrophy (SMA). In another specific embodiment, the subject is a human with SMA caused by an inactivating mutation or deletion in the SMN1 gene on both chromosomes, resulting in a loss of SMN1 gene function.

The term "spinal muscular atrophy" (or SMA) relates to a disease caused by an inactivating mutation or deletion in the SMN1 gene on both chromosomes, resulting in a loss of SMN1 gene function. Symptoms of SMA—depending on the type of SMA—include muscle weakness, poor muscle tone, weak cry, weak cough, limpness or a tendency to flop, difficulty sucking or swallowing, difficulty breathing, accumulation of secretions in the lungs or throat, clenched fists with sweaty hand, flickering/vibrating of the tongue, head often tilted to one side, even when lying down, legs that tend to be weaker than the arms, legs frequently assuming a "frog legs" position, feeding difficulties, increased susceptibility to respiratory tract infections, bowel/bladder weakness, lower-than-normal weight, inability to sit without support, failure to walk, failure to crawl, and hypotonia, areflexia, and multiple congenital contractures (arthrogryposis) associated with loss of anterior horn cells.

The term "treating spinal muscular atrophy (SMA)" or "treatment of spinal muscular atrophy (SMA)" includes one or more of the following effects: (i) reduction or amelioration of the severity of SMA; (ii) delay of the onset of SMA; (iii) inhibition of the progression of SMA; (iv) reduction of hospitalization of a subject; (v) reduction of hospitalization length for a subject; (vi) increase of the survival of a subject; (vii) improvement of the quality of life of a subject; (viii) reduction of the number of symptoms associated with SMA; (ix) reduction of or amelioration of the severity of one or more symptoms associated with SMA; (x) reduction of the duration of a symptom associated with SMA; (xi) prevention of the recurrence of a symptom associated with SMA; (xii) inhibition of the development or onset of a symptom of SMA; and/or (xiii) inhibition of the progression of a symptom associated with SMA. More particular, "treating SMA" denotes one or more of the following beneficial effects: (i) a reduction in the loss of muscle strength; (ii) an increase in muscle strength; (iii) a reduction in muscle atrophy; (iv) a reduction in the loss of motor function; (v) an increase in motor neurons; (vii) a reduction in the loss of motor neurons; (viii) protection of SMN deficient motor neurons from degeneration; (ix) an increase in motor function; (x) an increase in pulmonary function; and/or (xi) a reduction in the loss of pulmonary function.

In detail, "treating SMA" results in the functional ability or helps retain the functional ability for a human infant or a human toddler to sit up unaided or for a human infant, a human toddler, a human child or a human adult to stand up unaided, to walk unaided, to run unaided, to breathe unaided, to turn during sleep unaided, or to swallow unaided.

The term "mg/kg" refers to the dose in milligram of 7-(4,7-diazaspiro[2.5]octan-7-yl)-2-(2,8-dimethylimidazo[1,2-b]pyridazin-6-yl)pyrido[1,2-a]pyrimidin-4-one being used per kilogram of body weight of the subject to be treated. For example, 0.25 mg/kg means a dose of 0.25 milligram of 7-(4,7-diazaspiro[2.5]octan-7-yl)-2-(2,8-dimethylimidazo[1,2-b]pyridazin-6-yl)pyrido[1,2-a]pyrimidin-4-one per kilogram of body weight of the patient to be treated.

The term "patient" refers to a human (such as a male or female human) who has been diagnosed with SMA.

The term "active pharmaceutical ingredient" (or "API") denotes the compound or molecule in a pharmaceutical composition that has a particular biological activity.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "pharmaceutical composition" refers to a preparation which is in such form as to permit the biological activity of an active ingredient contained therein to be effective, and which contains no additional components which are unacceptably toxic to a subject to which the composition would be administered. The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "buffer" or "buffer system" denotes a pharmaceutically acceptable excipient or excipient mixture, which stabilizes the pH of a pharmaceutical preparation. Suitable buffers are well known in the art and can be found in the literature. Particular pharmaceutically acceptable buffers comprise citric buffer, malate buffer, maleate buffer, or tartrate buffer, most particularly tartrate buffer. Particular buffer systems of the invention combinations of organic acid and selected salts thereof, e.g. tribasic sodium citrate and citric acid, malic acid and sodium malate, potassium sodium tartrate and tartaric acid, or disodium tartrate and tartaric acid, particularly potassium sodium tartrate and tartaric acid. Alternatively, the organic acid (particularly tartaric acid) can be employed alone as "acidifier" instead of the combination of acid and the corresponding salt. Independently from the buffer used, the pH can be adjusted with an acid or a base known in the art, e.g. hydrochloric acid, acetic acid, phosphoric acid, sulfuric acid and citric acid, sodium hydroxide and potassium hydroxide. Particular acidifier is tartaric acid.

A "pharmaceutically acceptable carrier" refers to an ingredient in a pharmaceutical composition, other than an active ingredient, which is nontoxic to a subject. A pharmaceutically acceptable carrier includes, but is not limited to, a buffer or acidifier, excipient, stabilizer, or preservative.

The term "antioxidant" denotes pharmaceutically acceptable excipients, which prevent oxidation of the active pharmaceutical ingredient. Antioxidants comprise ascorbic acid, glutathione, cysteine, methionine, citric acid, EDTA.

The term "surfactant" denotes a pharmaceutically acceptable excipient which is used to protect protein compositions against mechanical stresses like agitation and shearing. Examples of pharmaceutically acceptable surfactants include poloxamers, polysorbates, polyoxyethylene alkyl ethers (BRIJ®), alkylphenylpolyoxyethylene ethers (TRITON-X®) or sodium dodecyl sulfate (SDS).

The term "poloxamer" denotes non-ionic triblock copolymers composed of a central hydrophobic chain of poly(propylene oxide) (PPO) flanked by two hydrophilic chains of poly(ethylene oxide) (PEO), each PPO or PEO chain can be of different molecular weights. Poloxamers are also known by the trade name Pluronics. Particular Poloxamer is Poloxamer 188, a poloxamer wherein the PPO chain has a molecular mass of 1800 g/mol and a PEO content of 80% (w/w).

The term "polysorbate" denotes oleate esters of sorbitol and its anhydrides, typically copolymerized with ethylene oxide. Particular polysorbates are Polysorbate 20 (poly(ethylene oxide) (20) sorbitan monolaurate, TWEEN 20®) or Polysorbate 80 (poly(ethylene oxide) (80) sorbitan monolaurate, TWEEN 80®).

The "hydrophilic-lipophilic balance" (HLB) value denotes the degree of hydrophilicity of a non-ionic surfactant. The HLB value is determined by the ratio between the molecular mass of the hydrophilic portion of the surfactant molecule and its overall molecular mass, as described by Griffin W. C., Journal of the Society of Cosmetic Chemists (1949) 1:311.

The term "hydrophilic" denotes the capacity of a molecule or portion of a molecule to interact with polar solvents, in particular with water, or with other polar moieties driven by hydrogen bonding, dipole-ion interactions and/or dipole-dipole interactions.

The terms "lipophilic" and "hydrophobic" can be used interchangeably and denote the tendency of a molecule or portion of a molecule to dissolve in non-polar environment such as fats, oils, and non-polar solvents driven by London dispersion forces.

The term "$C_{max}$" (expressed in units of pg/mL) means maximum observed plasma concentration and refers herein to that of colchicine.

The term "$T_{max}$" (expressed in units of hours, or as a median number of hours for $T_{max}$ in the study population) means the observed time to reach $C_{max}$ following drug administration; if it occurs at more than one time point $T_{max}$ is defined as the first time point with this value.

The term "$AUC_{T0-24h}$" (expressed in units of pg·h/mL) means the cumulative area under the plasma time concentration curve (AUC) calculated using the trapezoidal method from time 0 to 24 h.

The term "sdOCT" refers to spectral domain. optical coherence tomography.

The term "NOAEL" refers to No observed adverse effect level. In other words, the term NOAEL refers to the greatest concentration or amount of a substance, found by experiment or observation, which causes no detectable adverse alteration of morphology, functional capacity, growth, development, or life span of the patient under defined conditions of exposure The term "NOEL" is no observed effect level.

The term "ERG" refers to electroretinogram. An electroretinogram is waveform generated by measuring the variation in the electrical potential of the cornea upon photic (light) stimulation. Generally, direct and ground electrodes are applied on or near the subject cornea to record the electrical potential.

The term "FoxM1" refers to Forkhead box protein M1 (previously termed HFH11). FOXM1 gene is now known as a human proto-oncogene.

The term "MADD" refers to MAP-kinase activating death domain. 7-(4,7-diazaspiro[2.5]octan-7-yl)-2-(2,8-dimethylimidazo[1,2-b]pyridazin-6-yl)pyrido[1,2-a]pyrimidin-4-one according to the present invention refers to a compound of formula (I)

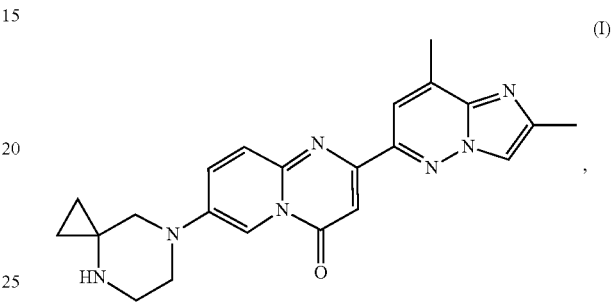

also known as RG7916, RO7034067, CAS Number 1825352-65-5, Methods of making and using the compound are described in EP3143025 A1.

Methods of making and using the pharmaceutical composition are described in WO2017080967 A1.

In one embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of SMA at 0.25 mg/kg for patient with a body weight of less than 20 kg and at 5 mg for patient with a body weight of more than or equal to 20 kg.

In a particular embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of SMA in patient (in particular a patient in need thereof), particularly wherein the patient is a human (such as a male or female human), at 0.25 mg/kg for patients with a body weight of less than 20 kg and at 5 mg for patients with a body weight of more than or equal to 20 kg.

In a particular embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of SMA in patient (in particular a patient in need thereof), particularly wherein the patient is a human (such as a male or female human), at 0.25 mg/kg once a day for patients with a body weight of less than 20 kg and at 5 mg once day for patients with a body weight of more than or equal to 20 kg.

In a more particular embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of type II SMA or/and type III SMA in patient (in particular a patient in need thereof), particularly wherein the patient is a human (such as a male or female human), at 0.25 mg/kg for patients with a body weight of less than 20 kg and at 5 mg for patients with a body weight of more than or equal to 20 kg.

In a more particular embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of type II SMA or type III SMA in patient (in particular a patient in need thereof), particularly wherein the patient is a human (such as a male or female human), at 0.25 mg/kg for patients with a body weight of less than 20 kg and at 5 mg for patients with a body weight of more than or equal to 20 kg.

In a more particular embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of type II SMA and type III SMA in patient (in particular a patient in need thereof), particularly wherein the patient is a human (such as a male or female human), at 0.25 mg/kg for patients with a body weight of less than 20 kg and at 5 mg for patients with a body weight of more than or equal to 20 kg.

In a more particular embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of type II SMA in patient (in particular a patient in need thereof), particularly wherein the patient is a human (such as a male or female human), at 0.25 mg/kg for patients with a body weight of less than 20 kg and at 5 mg for patients with a body weight of more than or equal to 20 kg.

In a more particular embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of type III SMA in patient (in particular a patient in need thereof), particularly wherein the patient is a human (such as a male or female human), at 0.25 mg/kg for patients with a body weight of less than 20 kg and at 5 mg for patients with a body weight of more than or equal to 20 kg.

Most particularly, 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of SMA, particularly type II SMA or/and type III SMA, at 0.25 mg/kg for patients with a body weight of less than 20 kg and at 5 mg for patients with a body weight of more than or equal to 20 kg In another embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of SMA, wherein 7-(4,7-diazaspiro[2.5]octan-7-yl)-2-(2,8-dimethylimidazo[1,2-b]pyridazin-6-yl)pyrido[1,2-a]pyrimidin-4-one is being administered, in particular administered orally at 0.25 mg/kg for patients with a body weight of less than 20 kg and at 5 mg for patients with a body weight of more than or equal to 20 kg.

In a particular embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of SMA in patient (in particular a patient in need thereof), particularly wherein the patient is a human (such as a male or female human), wherein 7-(4,7-diazaspiro[2.5]octan-7-yl)-2-(2,8-dimethylimidazo[1,2-b]pyridazin-6-yl)pyrido[1,2-a]pyrimidin-4-one is being administered, in particular administered orally at 0.25 mg/kg for patients with a body weight of less than 20 kg and at 5 mg for patients with a body weight of more than or equal to 20 kg.

In a more particular embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of type II SMA or/and type III SMA in patient (in particular a patient in need thereof), particularly wherein the patient is a human (such as a male or female human), wherein 7-(4,7-diazaspiro[2.5]octan-7-yl)-2-(2,8-dimethylimidazo[1,2-b]pyridazin-6-yl)pyrido[1,2-a]pyrimidin-4-one is being administered, in particular administered orally at 0.25 mg/kg for patients with a body weight of less than 20 kg and at 5 mg for patients with a body weight of more than or equal to 20 kg.

In a more particular embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of type II SMA or type III SMA in patient (in particular a patient in need thereof), particularly wherein the patient is a human (such as a male or female human), wherein 7-(4,7-diazaspiro[2.5]octan-7-yl)-2-(2,8-dimethylimidazo[1,2-b]pyridazin-6-yl)pyrido[1,2-a]pyrimidin-4-one is being administered, in particular administered orally at 0.25 mg/kg for patients with a body weight of less than 20 kg and at 5 mg for patients with a body weight of more than or equal to 20 kg.

In a more particular embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of type II SMA and type III SMA in patient (in particular a patient in need thereof), particularly wherein the patient is a human (such as a male or female human), wherein 7-(4,7-diazaspiro[2.5]octan-7-yl)-2-(2,8-dimethylimidazo[1,2-b]pyridazin-6-yl)pyrido[1,2-a]pyrimidin-4-one is being administered, in particular administered orally at 0.25 mg/kg for patients with a body weight of less than 20 kg and at 5 mg for patients with a body weight of more than or equal to 20 kg.

In a more particular embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of type II SMA in patient (in particular a patient in need thereof), particularly wherein the patient is a human (such as a male or female human), wherein 7-(4,7-diazaspiro[2.5]octan-7-yl)-2-(2,8-dimethylimidazo[1,2-b]pyridazin-6-yl)pyrido[1,2-a]pyrimidin-4-one is being administered, in particular administered orally at 0.25 mg/kg for patients with a body weight of less than 20 kg and at 5 mg for patients with a body weight of more than or equal to 20 kg.

In a more particular embodiment, the invention provides 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of type III SMA in patient (in particular a patient in need thereof), particularly wherein the patient is a human (such as a male or female human), wherein 7-(4,7-diazaspiro[2.5]octan-7-yl)-2-(2,8-dimethylimidazo[1,2-b]pyridazin-6-yl)pyrido[1,2-a]pyrimidin-4-one is being administered, in particular administered orally at 0.25 mg/kg for patients with a body weight of less than 20 kg and at 5 mg for patients with a body weight of more than or equal to 20 kg. More particularly, 7-(4,7-diazaspiro[2.5]octan-7-yl)-2-(2,8-dimethylimidazo[1,2-b]pyridazin-6-yl)pyrido[1,2-a]pyrimidin-4-one for use in the treatment of SMA, particularly type II SMA or/and type III SMA, at 0.25 mg/kg for patients with a body weight of less than 20 kg and at 5 mg for patients with a body weight of more than or equal to 20 kg.

In one embodiment, the invention provides a method for the treatment of spinal muscular atrophy (SMA), comprising administering to a patient (in particular a patient in need thereof), particularly wherein the patient is a human (such as a male or female human), 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg for patients with a body weight of less than 20 kg and at 5 mg for patients with a body weight of more than or equal to 20 kg. Particularly, the invention provides a method for the treatment of spinal muscular atrophy (SMA), comprising administering to a patient (in particular a patient in need thereof), particularly wherein the patient is a human (such as a male or female human), by oral administration 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg for patients with a body weight of less than 20 kg and at 5 mg for patients with a body weight of more than or equal to 20 kg.

In a particular embodiment, the invention provides a method for the treatment of spinal muscular atrophy (SMA), comprising administering to a patient (in particular a patient in need thereof), particularly wherein the patient is a human (such as a male or female human), 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg per day for patients with a body weight of less than 20 kg and at 5 mg per day for patients with a body weight of more than or equal to 20 kg. More particularly, the invention provides a method for the treatment of spinal muscular atrophy (SMA), comprising administering to a patient (in particular a patient in need thereof) particularly wherein the patient is a human (such as a male or female human), by oral administration 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg per day for patients with a body weight of less than 20 kg and at 5 mg per day for patients with a body weight of more than or equal to 20 kg. Most particularly the invention provides a method for the treatment of SMA, wherein 7-(4,7-diazaspiro[2.5]octan-7-yl)-2-(2,8-dimethylimidazo[1,2-b]pyridazin-6-yl)pyrido[1,2-a]pyrimidin-4-one is administered once a day.

In a further particular embodiment, the invention provides a method for the treatment of type II SMA or/and type III SMA, comprising administering to a patient (in particular a patient in need thereof), particularly wherein the patient is a human (such as a male or female human), 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg per day for patients with a body weight of less than 20 kg and at 5 mg per day for patients with a body weight of more than or equal to 20 kg. More particularly, the invention provides a method for the treatment of type II SMA or/and type III SMA, comprising administering to a patient (in particular a patient in need thereof), particularly wherein the patient is a human (such as a male or female human), by oral administration 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg per day for patients with a body weight of less than 20 kg and at 5 mg per day for patients with a body weight of more than or equal to 20 kg.

In an another particular embodiment, the invention provides a method for the treatment of type II SMA or type III SMA, comprising administering to a patient (in particular a patient in need thereof), particularly wherein the patient is a human (such as a male or female human), 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg per day for patients with a body weight of less than 20 kg and at 5 mg per day for patients with a body weight of more than or equal to 20 kg. More particularly, the invention provides a method for the treatment of type II SMA or type III SMA, comprising administering to a patient (in particular a patient in need thereof), particularly wherein the patient is a human (such as a male or female human), by oral administration 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg per day for patients with a body weight of less than 20 kg and at 5 mg per day for patients with a body weight of more than or equal to 20 kg.

In an another particular embodiment, the invention provides a method for the treatment of type II SMA and type III SMA, comprising administering to a patient (in particular a patient in need thereof), particularly wherein the patient is a human (such as a male or female human), 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg per day for patients with a body weight of less than 20 kg and at 5 mg per day for patients with a body weight of more than or equal to 20 kg. More particularly, the invention provides a method for the treatment of type II SMA and type III SMA, comprising administering to a patient (in particular a patient in need thereof), particularly wherein the patient is a human (such as a male or female human), by oral administration 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg per day for patients with a body weight of less than 20 kg and at 5 mg per day for patients with a body weight of more than or equal to 20 kg.

In an another particular embodiment, the invention provides a method for the treatment of type II SMA, comprising administering to a patient (in particular a patient in need thereof), particularly wherein the patient is a human (such as a male or female human), 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg per day for patients with a body weight of less than 20 kg and at 5 mg per day for patients with a body weight of more than or equal to 20 kg. More particularly, the invention provides a method for the treatment of type II SMA, comprising administering to a patient (in particular a patient in need thereof), particularly wherein the patient is a human, such as a male or female human, particularly wherein the patient is a human (such as a male or female human), by oral administration 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg per day for patients with a body weight of less than 20 kg and at 5 mg per day for patients with a body weight of more than or equal to 20 kg In an another particular embodiment, the invention provides a method for the treatment of type III SMA, comprising administering to a patient (in particular a patient in need thereof), particularly wherein the patient is a human (such as a male or female human), 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg per day for patients with a body weight of less than 20 kg and at 5 mg per day for patients with a body weight of more than or equal to 20 kg. More particularly, the invention provides a method for the treatment of type III SMA, comprising administering to a patient (in particular a patient in need thereof), particularly wherein the patient is a human (such as a male or female human), by oral administration 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg per day for patients with a body weight of less than 20 kg and at 5 mg per day for patients with a body weight of more than or equal to 20 kg.

In another embodiment, the invention provides a method for the treatment of spinal muscular atrophy (SMA), in a patient (in particular a patient in need thereof), particularly wherein the patient is a human (such as a male or female human), which comprises administering 0.25 mg per kilogram of body weight of 7-(4,7-diazaspiro[2.5]octan-7-yl)-

2-(2,8-dimethylimidazo[1,2-b]pyridazin-6-yl)pyrido[1,2-a]pyrimidin-4-one for a patient with a body weight of less than 20 kg. Particularly, the invention provides a method for the treatment of spinal muscular atrophy (SMA), in a patient (in particular a patient in need thereof), particularly wherein the patient is a human (such as a male or female human), which comprises administering 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one per day for a patient with a body weight of less than 20 kg.

In another embodiment, the invention provides a method for the treatment of spinal muscular atrophy (SMA), in a patient (in particular a patient in need thereof), particularly wherein the patient is a human (such as a male or female human), which comprises administering orally 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for a patient with a body weight of less than 20 kg. Particularly, the invention provides a method for the treatment of spinal muscular atrophy (SMA), in a patient (in particular a patient in need thereof), particularly wherein the patient is a human (such as a male or female human), which comprises administering orally 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one per day for a patient with a body weight of less than 20 kg.

In another embodiment, the invention provides a method for the treatment of spinal muscular atrophy (SMA), in a patient (in particular a patient in need thereof), particularly wherein the patient is a human (such as a male or female human), which comprises administering a dose of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for a patient with a body weight of less than 20 kg. Particularly, the invention provides a method for the treatment of spinal muscular atrophy (SMA), in a patient (in particular a patient in need thereof), particularly wherein the patient is a human (such as a male or female human), which comprises administering a dose of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one per day for a patient with a body weight of less than 20 kg.

In another embodiment, the invention provides a method for the treatment of spinal muscular atrophy (SMA), in a patient (in particular a patient in need thereof), particularly wherein the patient is a human (such as a male or female human), which comprises administering orally a dose of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one. Particularly, the invention provides a method for the treatment of spinal muscular atrophy (SMA), in a patient (in particular a patient in need thereof), particularly wherein the patient is a human (such as a male or female human), which comprises administering orally a dose of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one per day for a patient with a body weight of less than 20 kg.

In another embodiment, the invention provides a method for the treatment of spinal muscular atrophy (SMA), in a patient (in particular a patient in need thereof), particularly wherein the patient is a human (such as a male or female human), which comprises administering a dosage of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for a patient with a body weight of less than 20 kg. Particularly, the invention provides a method for the treatment of spinal muscular atrophy (SMA), in a patient (in particular a patient in need thereof), particularly wherein the patient is a human (such as a male or female human), which comprises administering a dose of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one per day for a patient with a body weight of less than 20 kg.

In another embodiment, the invention provides a method for the treatment of spinal muscular atrophy (SMA), in a patient (in particular a patient in need thereof), particularly wherein the patient is a human (such as a male or female human), which comprises administering orally a dosage of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for a patient with a body weight of less than 20 kg. Particularly, the invention provides a method for the treatment of spinal muscular atrophy (SMA), in a patient (in particular a patient in need thereof), particularly wherein the patient is a human (such as a male or female human), which comprises administering orally a dose of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one per day for a patient with a body weight of less than 20 kg.

In another embodiment, the invention provides a method for the treatment of spinal muscular atrophy (SMA), in a patient (in particular a patient in need thereof), particularly wherein the patient is a human (such as a male or female human), which comprises administering 5 mg of 7-(4,7-diazaspiro[2.5]octan-7-yl)-2-(2,8-dimethylimidazo[1,2-b]pyridazin-6-yl)pyrido[1,2-a]pyrimidin-4-one for a patient with a body weight of more than or equal to 20 kg. Particularly, the invention provides a method for the treatment of spinal muscular atrophy (SMA), in a patient (in particular a patient in need thereof), particularly wherein the patient is a human (such as a male or female human), which comprises administering 5 mg of 7-(4,7-diazaspiro[2.5]octan-7-yl)-2-(2,8-dimethylimidazo[1,2-b]pyridazin-6-yl)pyrido[1,2-a]pyrimidin-4-one per day for a patient with a body weight of more than or equal to 20 kg.

In another embodiment, the invention provides a method for the treatment of spinal muscular atrophy (SMA), in a patient (in particular a patient in need thereof), particularly wherein the patient is a human (such as a male or female human), which comprises administering orally 5 mg of 7-(4,7-diazaspiro[2.5]octan-7-yl)-2-(2,8-dimethylimidazo[1,2-b]pyridazin-6-yl)pyrido[1,2-a]pyrimidin-4-one for a patient with a body weight of more than or equal to 20 kg. Particularly, the invention provides a method for the treatment of spinal muscular atrophy (SMA), in a patient (in particular a patient in need thereof), particularly wherein the patient is a human (such as a male or female human), which comprises administering orally 5 mg of 7-(4,7-diazaspiro[2.5]octan-7-yl)-2-(2,8-dimethylimidazo[1,2-b]pyridazin-6-yl)pyrido[1,2-a]pyrimidin-4-one per day for a patient with a body weight of more than or equal to 20 kg.

In another embodiment, the invention provides a method for the treatment of spinal muscular atrophy (SMA), in a patient (in particular a patient in need thereof), particularly wherein the patient is a male or female human), which comprises administering a dose of 05 mg of 7-(4,7-diazaspiro[2.5]octan-7-yl)-2-(2,8-dimethylimidazo[1,2-b]pyridazin-6-yl)pyrido[1,2-a]pyrimidin-4-one for a patient with a body weight of more than or equal to 20 kg. Particularly, the invention provides a method for the treatment of spinal muscular atrophy (SMA), in a patient (in particular a patient in need thereof), particularly wherein the patient is a human (such as a male or female human), which comprises administering a dose of 5 mg of 7-(4,7-diazaspiro[2.5]octan-7-yl)-2-(2,8-dimethylimidazo[1,2-b]pyridazin-6-yl)pyrido[1,2-a]pyrimidin-4-one per day for a patient with a body weight of more than or equal to 20 kg.

In another embodiment, the invention provides a method for the treatment of spinal muscular atrophy (SMA), in a patient (in particular a patient in need thereof), particularly wherein the patient is a human (such as a male or female human), which comprises administering orally a dose of 5 mg of 7-(4,7-diazaspiro[2.5]octan-7-yl)-2-(2,8-dimethyl-imidazo[1,2-b]pyridazin-6-yl)pyrido[1,2-a]pyrimidin-4-one. Particularly, the invention provides a method for the treatment of spinal muscular atrophy (SMA), in a patient (in particular a patient in need thereof), particularly wherein the patient is a human (such as a male or female human), which comprises administering orally a dose of 5 mg of 7-(4,7-diazaspiro[2.5]octan-7-yl)-2-(2,8-dimethylimidazo[1,2-b]pyridazin-6-yl)pyrido[1,2-a]pyrimidin-4-one per day for a patient with a body weight of more than or equal to 20 kg.

In another embodiment, the invention provides a method for the treatment of spinal muscular atrophy (SMA), in a patient (in particular a patient in need thereof), particularly wherein the patient is a human (such as a male or female human), which comprises administering a dosage of 5 mg of 7-(4,7-diazaspiro[2.5]octan-7-yl)-2-(2,8-dimethylimidazo[1,2-b]pyridazin-6-yl)pyrido[1,2-a]pyrimidin-4-one for a patient with a body weight of more than or equal to 20 kg. Particularly, the invention provides a method for the treatment of spinal muscular atrophy (SMA), in a patient (in particular a patient in need thereof), particularly wherein the patient is a human (such as a male or female human), which comprises administering a dose of 5 mg of 7-(4,7-diazaspiro[2.5]octan-7-yl)-2-(2,8-dimethylimidazo[1,2-b]pyridazin-6-yl)pyrido[1,2-a]pyrimidin-4-one per day for a patient with a body weight of more than or equal to 20 kg.

In another embodiment, the invention provides a method for the treatment of spinal muscular atrophy (SMA), in a patient (in particular a patient in need thereof), particularly wherein the patient is a human (such as a male or female human), which comprises administering orally a dosage of 5 mg of 7-(4,7-diazaspiro[2.5]octan-7-yl)-2-(2,8-dimethyl-imidazo[1,2-b]pyridazin-6-yl)pyrido[1,2-a]pyrimidin-4-one for a patient with a body weight of more than or equal to 20 kg. Particularly, the invention provides a method for the treatment of spinal muscular atrophy (SMA), in a patient (in particular a patient in need thereof), particularly wherein the patient is a human (such as a male or female human), which comprises administering orally a dose of 5 mg of 7-(4,7-diazaspiro[2.5]octan-7-yl)-2-(2,8-dimethylimidazo[1,2-b]pyridazin-6-yl)pyrido[1,2-a]pyrimidin-4-one per day for a patient with a body weight of more than or equal to 20 kg.

In a further embodiment, the invention provides a method of treating spinal muscular atrophy (SMA), comprising administering to a patient 7-(4,7-diazaspiro[2.5]octan-7-yl)-2-(2,8-dimethylimidazo[1,2-b]pyridazin-6-yl)pyrido[1,2-a]pyrimidin-4-one at 0.25 mg/kg for patient with a body weight of less than 20 kg and at 5 mg for patients with a body weight of more than or equal to 20 kg.

In another embodiment, the invention provides a pharmaceutical composition for use in the treatment of SMA (more particularly type II or/and type III SMA), which comprises 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one, being administered, in particular orally administered once a day, for patients with a body weight of less than 20 kg.

In another embodiment, the invention provides a pharmaceutical composition for use in the treatment of SMA (more particularly type II or/and type III SMA), which comprises 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one being administered, in particular orally administered once a day for patients with a body weight of less than 20 kg.

In another embodiment, the invention provides a pharmaceutical composition for use in the treatment of SMA (more particularly type II or/and type III SMA), which comprises 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one being administered, in particular orally administered once a day for patients with a body weight of less than 20 kg.

In another embodiment, the invention provides a pharmaceutical composition for use in the treatment of SMA (more particularly type II or/and type III SMA), which comprises 5 mg of 7-(4,7-diazaspiro[2.5]octan-7-yl)-2-(2,8-dimethylimidazo[1,2-b]pyridazin-6-yl)pyrido[1,2-a]pyrimidin-4-one, being administered, in particular orally administered once a day, for patients with a body weight of more than or equal to 20 kg.

In another embodiment, the invention provides a pharmaceutical composition for use in the treatment of SMA (more particularly type II or/and type III SMA), which comprises 5 mg of 7-(4,7-diazaspiro[2.5]octan-7-yl)-2-(2,8-dimethylimidazo[1,2-b]pyridazin-6-yl)pyrido[1,2-a]pyrimidin-4-one being administered, in particular orally administered once a day for patients with a body weight of more than or equal to 20 kg.

In another embodiment, the invention provides a pharmaceutical composition for use in the treatment of SMA (more particularly type II or/and type III SMA), which comprises 5 mg of 7-(4,7-diazaspiro[2.5]octan-7-yl)-2-(2,8-dimethylimidazo[1,2-b]pyridazin-6-yl)pyrido[1,2-a]pyrimidin-4-one being administered, in particular orally administered once a day for patients with a body weight of more than or equal to 20 kg.

The pharmaceutical composition can be used to treat spinal muscular atrophy (SMA), in particular type II SMA and type III SMA, in a patient, especially a human (i. e., a male or female human).

It has been found, that 7-(4,7-diazaspiro[2.5]octan-7-yl)-2-(2,8-dimethylimidazo[1,2-b]pyridazin-6-yl)pyrido[1,2-a]pyrimidin-4-one of present invention has a high aqueous solubility. Due to the handicaps in swallowing of all age groups of SMA patients, administration of a solution has been found to be preferred.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]

pyrimidin-4-one formulated as oral aqueous solution by dissolving the 7-(4,7-diazaspiro[2.5]octan-7-yl)-2-(2,8-dimethylimidazo[1,2-b]pyridazin-6-yl)pyrido[1,2-a]pyrimidin-4-one in a buffer system at pH of less than pH 4, particularly less than pH 3.8, more particularly less than pH 3.6, most particularly pH 3.0 to 3.2, in order to provide sufficiently high drug concentration, e.g. citric buffer system, malate buffer system, maleate buffer system, or tartrate buffer system, most particularly tartrate buffer system.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one as a dry powder or granulation for constitution of an oral solution. A buffer system can be incorporated into dry formulation by the selection of organic acid and salts thereof as fine powders, e.g. tribasic sodium citrate and citric acid, disodium malate and malic acid, potassium sodium tartrate and tartaric acid, or disodium tartrate and tartaric acid, particularly potassium sodium tartrate and tartaric acid. Alternatively, the organic acid (particularly tartaric acid) can be employed alone as acidifier instead of the combination of acid and the corresponding salt.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one, a diluent, such as sorbitol, isomalt, or particularly mannitol, and combinations thereof, which ensure fast dissolution of the powder blend during constitution of the oral solution. Optionally, filler can be added to be granulated by dry compaction in order to improve the flowability and to ensure robust uniformity.

Ingredients for the constitution of a solvent system for 7-(4,7-diazaspiro[2.5]octan-7-yl)-2-(2,8-dimethylimidazo[1,2-b]pyridazin-6-yl)pyrido[1,2-a]pyrimidin-4-one can be formulated as separate formulation. The constituted solvent can be used for dissolution of 7-(4,7-diazaspiro[2.5]octan-7-yl)-2-(2,8-dimethylimidazo[1,2-b]pyridazin-6-yl)pyrido[1,2-a]pyrimidin-4-one in a bottle at the start of the in-use period of the oral solution.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof in powder form for constitution of an oral solution.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof are filled in a multidose bottle with adapter for use of oral dispensers. It has been found that such multidose bottle with adapter for use of oral dispensers enables high dosing flexibility, e.g. body weight adjusted dosing and provides safe and convenient dose administration.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is prepared through dry granulation by roller compaction followed bottle filling. It has been found that such processing is beneficial (particularly for water soluble fillers) to prevent demixing.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof wherein the composition is an oral aqueous solution or a dry powder suitable for constitution of an oral aqueous solution.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido

[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof wherein the composition is an oral aqueous solution not including aerosols or a dry powder suitable for constitution of an oral aqueous solution.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is not an aerosol.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof does not comprise a tonicifier, e.g. a salt such as sodium chloride.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof wherein the composition is an oral aqueous solution or a dry powder suitable for constitution of an oral aqueous solution, and wherein the oral aqueous solution has a pH of less than pH4, particularly less than pH3.8, more particularly less than pH 3.6, most particularly pH 3.0 to 3.2.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof and a citrate, malate, maleate or tartrate buffer system, particularly a malate or tartrate buffer system, most particularly a tartrate buffer system; or alternatively the corresponding acid of a buffer system alone as acidifier, particularly tartaric acid; wherein the composition is an oral aqueous solution or a dry powder suitable for constitution of an oral aqueous solution.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof wherein the composition is an oral aqueous solution.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof wherein the composition is an oral aqueous solution in a buffer system at pH of less than pH4, particularly less than pH3.8, more particularly less than pH 3.6, most particularly pH 3.0 to 3.2.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof wherein the composition is an oral aqueous solution in a citrate, malate, maleate or tartrate buffer system, particularly in a malate or tartrate buffer system, most particularly in a tartrate buffer system; or alternatively the corresponding acid of a buffer system alone as acidifier, particularly tartaric acid.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof wherein the composition is dry powder suitable for constitution of an oral aqueous solution.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof wherein the composition is dry powder comprising a buffer system suitable for constitution of an oral aqueous solution at pH of less than pH4, particularly less than pH3.8, more particularly less than pH 3.6, most particularly pH 3.0 to 3.2.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof wherein the composition is dry powder comprising citrate, malate, maleate or tartrate buffer system, particularly in a malate or tartrate buffer system, most particularly in a tartrate buffer system; or alternatively the corresponding acid of a buffer system alone as acidifier, particularly tartaric acid; suitable for constitution of an oral aqueous solution.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof optionally further comprises an extragranular filler, such as lactose, starch, hydrolyzed starch, maltodextrin, microcrystalline cellulose, mannitol, sorbitol, sucrose, dextrose, dibasic calcium phosphate, calcium sulfate, or combinations thereof.

In a particular embodiment of the invention, the extragranular filler is sorbitol, isomalt, mannitol, or combinations thereof, particularly mannitol, more particularly crystalline mannitol, most particularly crystalline mannitol with mean diameter of 160 μm (Pearlitol® 160 C).

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof optionally further comprises a diluent, such as lactose, starch, hydrolyzed starch, maltodextrin, microcrystalline cellulose, mannitol, isomalt (E 953, (2ξ)-6-O-α-D-Glucopyranosyl-D-arabino-hexitol), sorbitol, sucrose, dextrose, dibasic calcium phosphate, calcium sulfate, or combinations thereof.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof optionally further comprises a diluent, such as lactose, starch, hydrolyzed starch, microcrystalline cellulose, mannitol, sorbitol, sucrose, dextrose, dibasic calcium phosphate, calcium sulfate, or combinations thereof.

In a particular embodiment of the invention, the diluent is mannitol, particularly D-mannitol suitable for direct compression such as Parteck® M100.

In a particular embodiment of the invention, the diluent is a mixture of mannitol and isomalt, particularly D-mannitol and (2)-6-O-α-D-Glucopyranosyl-D-arabino-hexitol).

Isomalt as second diluent has been found to improve the granule properties.

The constituted oral solution of the 7-(4,7-diazaspiro[2.5]octan-7-yl)-2-(2,8-dimethylimidazo[1,2-b]pyridazin-6-yl)pyrido[1,2-a]pyrimidin-4-one in a buffer can provide in-use times of more than or equal to two weeks by the use of stabilizers and antioxidants, such as vitamin A, vitamin C, vitamin E, vitamin E TPGS, retinyl palmitate, selenium, cysteine, methionine, citric acid, sodium citrate, methyl paraben, propyl paraben, disodium edetate, butyl hydroxyl toluol, riboflavin, ascorbic acid or combinations thereof.

The constituted oral solution of 7-(4,7-diazaspiro[2.5] octan-7-yl)-2-(2,8-dimethylimidazo[1,2-b]pyridazin-6-yl) pyrido[1,2-a]pyrimidin-4-one in a buffer can provide in-use times of more than or equal to two weeks by the use of stabilizers and antioxidants, such as vitamin E TPGS, disodium edetate, butyl hydroxyl toluol, riboflavin, ascorbic acid, or combinations thereof.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido [1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a] pyrimidin-4-one or a pharmaceutically acceptable salt thereof optionally further comprises a antioxidant and/or stabilizer, such as vitamin E TPGS (D-alpha tocopheryl polyethylene glycol 1000 succinate), disodium ethylenediaminetetraacetate (disodium edetate, $Na_2$ EDTA), butyl hydroxyl toluol, riboflavin, ascorbic acid, or combinations thereof. It has been found that a antioxidant and/or stabilizer can be beneficial for prolonged use time in multidose containers or to improve drug stability in solution over in-use period.

In a particular embodiment of the invention, the antioxidant is ascorbic acid ((5R)-[(1S)-1,2-dihydroxyethyl]-3,4-dihydroxyfuran-2(5H)-one).

In a particular embodiment of the invention, the stabilizer is disodium ethylenediaminetetraacetate (disodium edetate, $Na_2$ EDTA).

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido [1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1, 2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a] pyrimidin-4-one or a pharmaceutically acceptable salt thereof optionally further comprises a lubricant. It has been found that a lubricant can be used as processing aid for roller compaction. Further a lubricant can be used for water soluble ingredients such as PEG to ensure acceptability of appearance.

In a particular embodiment of the invention, the lubricant is poly(ethylene glycol), particularly poly(ethylene glycol) with number average molecular weight Mn 6,000 (PEG 6000).

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido [1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1, 2-a]pyrimidin-4-one for patients with a body weight of more than or equal to 20 kg, being administered, in particular orally administered once a day, wherein the pharmaceutical composition comprises 7-(4,7-diazaspiro[2.5]octan-7-yl)-2-(2,8-dimethylimidazo[1,2-b]pyridazin-6-yl)pyrido[1,2-a] pyrimidin-4-one or a pharmaceutically acceptable salt thereof optionally further comprises a sweetener and/or flavor to improve palatability.

In a particular embodiment of the invention, the flavor is strawberry flavor or vanilla flavor.

In a particular embodiment of the invention, the sweetener is sucralose (1,6-dichloro-1,6-dideoxy-β-D-fructofuranosyl-4-chloro-4-deoxy-α-D-galactopyranoside, E955) or sodium saccharin.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido [1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1, 2-a]pyrimidin-4-one for patients with a body weight of more than or equal to 20 kg, being administered, in particular orally administered once a day, wherein the pharmaceutical composition comprises:
  7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof; and
  a buffer system selected from citrate, malate, maleate or tartrate, particularly malate or tartrate, most particularly tartrate; or alternatively the corresponding acid of a buffer system alone as acidifier, particularly tartaric acid.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido [1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1, 2-a]pyrimidin-4-one for patients with a body weight of more than or equal to 20 kg, being administered, in particular orally administered once a day, wherein the pharmaceutical composition comprises:
  7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof;
  a buffer system, particularly a buffer system selected from citrate, malate, maleate or tartrate, more particularly malate or tartrate, most particularly tartrate; or alternatively the corresponding acid of a buffer system alone as acidifier, particularly tartaric acid; and
  a diluent, particularly mannitol or a mixture of mannitol and isomalt, more particularly mannitol.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido [1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1, 2-a]pyrimidin-4-one for patients with a body weight of more than or equal to 20 kg, being administered, in particular orally administered once a day, wherein the pharmaceutical composition comprises:

- 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof; and
- a diluent, particularly mannitol or a mixture of mannitol and isomalt, more particularly mannitol.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises:

- 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof;
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- an antioxidant, particularly ascorbic acid; and
- a stabilizer, particularly disodium edetate.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises:

- 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof;
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid; and
- a stabilizer, particularly disodium edetate.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises:

- 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof;
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid;
- a stabilizer, particularly disodium edetate; and
- a lubricant, particularly PEG6000.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises:

- 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof;
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid;
- a stabilizer, particularly disodium edetate;
- a lubricant, particularly PEG6000; and In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises:

- 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof;
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid;
- a stabilizer, particularly disodium edetate;
- a lubricant, particularly PEG6000;
- optionally a sweetener, particularly sucralose or sodium saccharin, most particularly sucralose; and
- optionally a flavor, particularly strawberry flavor or vanilla flavor.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises:
- 1 to 10% wt of 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof,
- 5 to 15% wt of a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- 40 to 70% wt of a diluent, particularly mannitol or a mixture of mannitol and isomalt, more particularly mannitol;
- 1 to 4% wt of an antioxidant, particularly ascorbic acid;
- 0.5 to 2% wt of a stabilizer, particularly disodium edetate;
- 0.5 to 2% w of a lubricant, particularly PEG6000;
- 0 to 3% wt of a sweetener, particularly sucralose or sodium saccharin, most particularly sucralose; and
- 0 to 20% wt of a flavor, particularly strawberry flavor or vanilla flavor;

wherein the total amount of ingredients does not exceed 100% wt.

In yet another embodiment, the invention provides a pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the pharmaceutical composition comprises:
- 2 to 6% wt of 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof,
- 9 to 13% wt of a tartrate buffer system;
- 45 to 55% wt of a mannitol as first diluent and 8 to 10% wt of isomalt as second diluent;
- 1 to 3% wt of ascorbic acid as antioxidant;
- 0.5 to 2% wt of disodium edetate as stabilizer;
- 0.5 to 2% w of PEG6000 as lubricant;
- 1.5 to 2% wt of sucralose as sweetener; and
- 13 to 17% wt of strawberry flavor;

wherein the total amount of ingredients does not exceed 100% wt.

In yet another embodiment, the invention provides a kit for the preparation of pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the kit comprises:
- a powder blend comprising 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof, and
- water as solvent for constitution.

In yet another embodiment, the invention provides a kit for the preparation of pharmaceutical composition for use in the treatment of SMA (more particularly type II or/and type III SMA), at 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, wherein the kit comprises:
- 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof,
- a powder blend as vehicle for constitution, and
- optionally water as solvent for constitution.

In particular, a power blend as vehicle suitable for constitution of 7-(4,7-diazaspiro[2.5]octan-7-yl)-2-(2,8-dimethylimidazo[1,2-b]pyridazin-6-yl)pyrido[1,2-a]pyrimidin-4-one as described herein or a pharmaceutically acceptable salt thereof, comprising:
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid; and
- a diluent, particularly mannitol or a mixture of mannitol and isomalt, more particularly mannitol.

In particular a power blend as vehicle suitable for constitution of 7-(4,7-diazaspiro[2.5]octan-7-yl)-2-(2,8-dimethylimidazo[1,2-b]pyridazin-6-yl)pyrido[1,2-a]pyrimidin-4-one as described herein or a pharmaceutically acceptable salt thereof, comprising:
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid;
- a stabilizer, particularly disodium edetate;
- a lubricant, particularly PEG6000; and In particular a power blend as vehicle suitable for constitution of 7-(4,7-diazaspiro[2.5]octan-7-yl)-2-(2,8-dimethylimidazo[1,2-b]pyridazin-6-yl)pyrido[1,2-a]pyrimidin-4-one as described herein or a pharmaceutically acceptable salt thereof, comprising:
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid;

a stabilizer, particularly disodium edetate;
a lubricant, particularly PEG6000;
optionally a sweetener, particularly sucralose or sodium saccharin, most particularly sucralose; and
optionally a flavor, particularly strawberry flavor or vanilla flavor.

In particular a power blend as vehicle suitable for constitution of 7-(4,7-diazaspiro[2.5]octan-7-yl)-2-(2,8-dimethylimidazo[1,2-b]pyridazin-6-yl)pyrido[1,2-a]pyrimidin-4-one as described herein or a pharmaceutically acceptable salt thereof, comprising:
   4 to 15% wt of a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
   40 to 70% wt of a diluent, particularly mannitol or a mixture of mannitol and isomalt, more particularly mannitol;
   1 to 4% wt of an antioxidant, particularly ascorbic acid;
   0.2 to 2% wt of a stabilizer, particularly disodium edetate;
   0.5 to 2% w of a lubricant, particularly PEG6000;
   0 to 3% wt of a sweetener, particularly sucralose or sodium saccharin, most particularly sucralose; and
   0 to 20% wt of a flavor, particularly strawberry flavor or vanilla flavor;
wherein the total amount of ingredients does not exceed 100% wt.

In particular, a power blend as vehicle suitable for constitution of 7-(4,7-diazaspiro[2.5]octan-7-yl)-2-(2,8-dimethylimidazo[1,2-b]pyridazin-6-yl)pyrido[1,2-a]pyrimidin-4-one as described herein or a pharmaceutically acceptable salt thereof, comprising:
   9 to 13% wt of a tartrate buffer system or tartaric acid;
   45 to 55% wt of a mannitol as first diluent and 8 to 10% wt of isomalt as second diluent;
   1 to 3% wt of ascorbic acid as antioxidant;
   0.3 to 0.9% wt of disodium edetate as stabilizer;
   0.5 to 2% w of PEG6000 as lubricant;
   0.8 to 2.0% wt of sucralose as sweetener; and
   7.5 to 19% wt of strawberry flavor;
wherein the total amount of ingredients does not exceed 100% wt.

In a particular embodiment, the invention provides a pharmaceutical composition for use in the treatment of SMA (more particularly type II or/and type III SMA), as described herein wherein the pharmaceutical composition is being administered orally once a day.

In another embodiment, the invention provides the use of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, for the treatment of SMA, in particular type II SMA or/and type III SMA.

In another embodiment, the invention provides the use of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, for the treatment of SMA, in particular type II SMA or/and type III SMA.

In a particular embodiment, the invention provides the use of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, for the treatment of SMA in patient (in particular a patient in need thereof), particularly wherein the patient is a human (such as a male or female human).

In a more particular embodiment, the invention provides the use of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, for the treatment of type II SMA or/and type III SMA in patient (in particular a patient in need thereof), particularly wherein the patient is a human (such as a male or female human).

In a more particular embodiment, the invention provides the use of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, for the treatment of type II SMA or type III SMA in patient (in particular a patient in need thereof), particularly wherein the patient is a human (such as a male or female human).

In a more particular embodiment, the invention provides the use of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, for the treatment of type II SMA and type III SMA in patient (in particular a patient in need thereof), particularly wherein the patient is a human (such as a male or female human).

In another embodiment, the invention provides the use of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, for the preparation of medicaments for the treatment of SMA, in particular type II SMA or/and type III SMA.

In a particular embodiment, the invention provides the use of 0.25 mg per kilogram of body weight of 7-(4,7-diazaspiro[2.5]octan-7-yl)-2-(2,8-dimethylimidazo[1,2-b]pyridazin-6- yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, for the preparation of medicaments for the treatment of SMA in patient (in particular a patient in need thereof), particularly wherein the patient is a human (such as a male or female human).

In a more particular embodiment, the invention provides the use of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, for the preparation of medicaments for the treatment of type II SMA or/and type III SMA in patient (in particular a patient in need thereof), particularly wherein the patient is a human (such as a male or female human).

In a more particular embodiment, the invention provides the use of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, for the preparation of medicaments for the treatment of type II SMA or type III SMA in patient (in particular a patient in need thereof), particularly wherein the patient is a human (such as a male or female human).

In a more particular embodiment, the invention provides the use of 0.25 mg per kilogram of body weight of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of less than 20 kg or 5 mg of 7-(4,7-diazaspiro[2.5]octan-7-yl)-2-(2,8-dimethylimidazo[1,2-b]pyridazin-6-yl)pyrido[1,2-a]pyrimidin-4-one for patients with a body weight of more than or equal to 20 kg, being administered, in particular orally administered once a day, for the preparation of medicaments for the treatment of type II SMA and type III SMA in patient (in particular a patient in need thereof), particularly wherein the patient is a human (such as a male or female human).

The patient according to the invention in particular is a human, more particularly a male or female human. The human can be of any race (e. g., Caucasian or Oriental).

In particular embodiments, the methods, the uses, pharmaceutical compositions in accordance with the present invention, 7-(4,7-diazaspiro[2.5]octan-7-yl)-2-(2,8-dimethylimidazo[1,2-b]pyridazin-6-yl)pyrido[1,2-a]pyrimidin-4-one is administered once a day.

The following example is intended merely to illustrate the practice of the present invention and is not provided by way of limitation.

EXAMPLE 1

Study BP39055 is a two-part operationally seamless, multi-center, randomized, placebo-controlled, double-blind study to investigate the safety, tolerability, pharmacokinetics (PK), pharmacodynamics (PD) and efficacy of RO7034067 in Type 2 and 3 spinal muscular atrophy (SMA) patients.

The study consists of an exploratory dose-finding part (Part 1) and a confirmatory part (Part 2).

The primary objective of Part 1 is to evaluate the safety, tolerability, PK and PD of RO7034067 in patients with Type 2 and Type 3 (ambulant or non-ambulant) SMA, and to select the dose for Part 2 of the study.

Part 1 was a double-blinded, placebo-controlled, randomized (2:1 RO7034067: placebo), exploratory dose-finding study in Type 2 and Type 3 (ambulant and non-ambulant) SMA patients. This will be followed by an open-label extension (OLE) at the same dose as selected for Part 2 of the study.

Part 1 of the study enrolled patients in two age groups:
Group A: adolescent and adult patients aged 12 25 years
Group B: children aged 2 11 years
RO7034067 dose levels were investigated in a staggered, dose escalation manner in both age groups.

As per protocol, the following steps were performed for the conduct of Part 1 of the study:

Enrolment into the study was initially opened to adult and adolescent patients (Cohort A1) receiving blinded RO7034067 3 mg once daily (first dose level as defined in the protocol, targeting an AUC0-24 h,ss of 700 ng□h/mL); 10 patients aged 12□16 years were enrolled in Cohort A1.

Once RO7034067 at this dose level was shown to be safe and well-tolerated for at least 4 weeks in 9 patients enrolled in Cohort A1 (minimum as per protocol was 3 patients aged 12□17 years on active treatment, which was ensured with a minimum of 6 patients and a randomization of 2:1), enrolment was opened to a cohort of younger patients (Cohort B1). The dose recommended by the IMC for this age group according to the target AUC0-24 h,ss of 700 ng□h/mL was 0.02 mg/kg (see IMC recommendation of 12 Dec. 2016 in Appendix 1); 10 patients aged 3-11 years were enrolled in Cohort B1.

At the same time point (i.e., once safety and tolerability were confirmed based on the review of at least 4 weeks of treatment at 3 mg once daily in 9 patients in Cohort A1), enrolment was opened to another cohort of 9 adult and adolescent patients (Cohort A2) receiving RO7034067 5 mg once daily (see IMC recommendation of 19 Jan. 2017 in Appendix 1). As per protocol, the higher dose level was determined such as to achieve maximum SMN protein increase, without exceeding the exposure cap (Cmax 400 ng/mL; mean AUC0 24 h,ss 2000 ng□h/mL); 10 patients aged 13□24 years were enrolled in Cohort A2.

Based on the review of a minimum of 4 weeks of treatment at 0.02 mg/kg in 9 patients enrolled in Cohort B1, the following recommendations were made by the IMC: i) to increase the dose in these patients to 0.05 mg/kg without exceeding a cap dose of 3 mg, and ii) to enroll a minimum of 9 additional patients aged 2□11 years at a dose of 0.05 mg/kg without exceeding a cap dose of 3 mg (Cohort B2), targeting at least 5 patients aged 2□6 years (see IMC recommendation of 13 Mar. 2017 in Appendix 1); 11 patients aged 2□6 years were enrolled in this additional cohort (Cohort B2).

Once RO7034067 was shown to be safe and well-tolerated for at least 4 weeks in 9 patients enrolled in Cohort B2 at the dose of 0.05 mg/kg, the recommendation was made by the IMC to increase the dose in all ongoing patients from Cohorts B1 and B2 to 0.15 mg/kg without exceeding a cap dose of 3 mg (see IMC recommendation of 23 May 2017 in Appendix 1). At the same time point, enrollment was opened to another cohort of 9 patients at the dose of 0.25 mg/kg without exceeding a cap dose of 5 mg (Cohort B3), determined such as to achieve maximum Survival of Motor Neuron (SMN) protein increase, without exceeding the exposure cap (Cmax 400 ng/mL; mean AUC0-24 h,ss 2000 ng·h/mL); 10 patients aged 2–11 years were enrolled in Cohort B3.

Upon completion of at least 12 weeks of placebo-controlled treatment by a minimum of 9 patients of each cohort, the IMC reviewed all available data from the cohort to make the decision to switch placebo patients to active treatment at the dose tested in their respective cohort. Dates of the IMC decisions to switch placebo patients to active treatment in the respective cohorts are provided in Section 1.3.

For the last cohort in Part 1 (Cohort B3), all available safety, tolerability, PK and PD data following completion of a minimum of 4 weeks treatment by the 9th patient (including all available data for the 10th patient of the last cohort who was enrolled approximately 1 week after the 9th patient, and all available data from all previous cohorts) were reviewed by the IMC in order to select the dose to be administered in Part 2 of the study. This dose selection was confirmed by the external iDMC following review of the same data package. The data on which this dose decision was based are summarized in this report.

Upon review of all available Part 1 data by the iDMC and confirmation of the IMC dose selection, Part 2 will start and all patients from Part 1 will be switched to the dose selected for Part 2, as part of the OLE phase of this study. Patients from the last cohort of Part 1 will need to complete treatment out to the end of the 12 week treatment period of their cohort before entering the OLE. Patients will continue to be followed up for safety, tolerability and efficacy as part of the OLE phase of the study in order to provide longer term data of RO7034067 treatment. These patients will not contribute to the confirmatory efficacy analyses conducted in Part 2 of the study.

A total of 51 patients were enrolled in Part 1 of the study. Patients were enrolled across 5 different centers (Italy [2 centers], Germany, France and Belgium). Patients were enrolled in five cohorts, which included patients on placebo and active treatment in a 1:2 ratio

|  | Adolescents and adult patients (12-25 yr) | | Children (2-11 yr) | | |
|---|---|---|---|---|---|
|  | Cohort 1a 3 mg | Cohort 1b 5 mg | Cohort 2a 0.02 mg/kg Dose increased to 0.15 mg/kg | Cohort 2b 0.05 mg/kg | Cohort 2c 0.25 mg/kg |
| n | 10 | 10 | 10 | 11 | 10 |
| Age | 13.5 [12-16] | 16.5 [13-24] | 6 [3-11] | 4 [2-6] | 5 [3-11] |
| Body weight (kg) | 38.6 [22.2-51.9] | 45.5 [21-79.5] | 16.7 [9-25.1] | 15 [9-20.6] | 15.7 [11.4-55.2] |
| SMA type | Type 2: n = 8 Type 3: n = 2 | Type 2: n = 3 Type 3: n = 6 Type 3(a): n = 1 | Type 2: n = 8 Type 3: n = 2 | Type 2: n = 7 Type 3(a): n = 4 | Type 2: n = 5 Type 3(a): n = 2 |
| SMN2 gene Copy number | 3: n = 10 | 2: n = 1 3: n = 8 4: n = 1 | 3: n = 10 | 3: n = 9 4: n = 2 | 3: n = 9 4: n = 1 |

The protocol defined the dose selection criteria for Part 2 of the study as a dose that, based on Part 1 data, appears safe and well tolerated, and is expected: i) to achieve an exposure resulting in a clinically relevant increase in Survival of Motor Neuron (SMN) protein in Type 2 and 3 SMA patients and ii) the mean AUC0 24 h,ss of RO7034067 (steady-state area under the curve between time zero and 24 hours after dose) has to stay below the exposure cap of 2000 ng·h/mL.

| Summary of estimated $AUC_{0-24\ h,ss}$ (ng*h/mL) of Sunfish Part 1 population Median [range] | | | |
|---|---|---|---|
| 12-25 yr | | 3 mg | 5 mg |
|  | | 1040 [703-1360] | 1610 [1140-1950] |
| 2-11 yr 0.02 mg/kg | 0.05 mg/kg | 0.15 mg/kg | 0.25 mg/kg |
| 133 [79.6-167] | 407 [237-493] | 822 [746-864] | 1450 [1230-2090] |

As defined in the study protocol, available data suggest that a 100% increase in SMN protein levels is indeed expected to turn more severe SMA phenotypes into milder forms, while further increase is likely to provide even greater benefit.

Summary of fold-increase from the baseline in SMN protein on Day 28: median [range]

| Placebo | 0.02 mg | 0.05 mg | 0.15 mg/kg | 0.25 mg/kg | 3 mg | 5 mg |
|---|---|---|---|---|---|---|
| 0.958 [0.714-1.38] | 1.09 [0.813-1.47] | 1.51 [0.97-2.30] | 1.67 [1.20-1.87] | 1.96 [1.17-2.50] | 2.25 [1.43-2.52] | 2.51 [1.49-3.51] |

EXAMPLE 2: (Taken from the BI § 4.1.2.2

Adult C/C-allele mice were treated for 10 days with vehicle or RO7034067 (1, 3 or 10 mg/kg per os [PO], daily), and PND3 SMNΔ7 mice were treated for 7 days with vehicle or RO7034067 (0.1, 0.3, 1 or 3 mg/kg intraperitoneal [IP], daily). R7034067 dose-dependently increased SMN protein levels in brain and muscle tissue, with a maximum effect of a 2-3 fold increase reached at 10 mg/kg in adult C/C allele mice and at 1-3 mg/kg in neonatal SMNΔ7 mice (FIGS. 1a and 1b). Thus, in the muscle of C/C-allele mice at the 10 mg/kg dose, the SMN levels achieved were no different from those in heterozygous mice. In SMNΔ7 mice, the SMN protein increase was only partial in both brain and muscle, reaching approximately 43% (brain) and 55% (muscle) of protein levels in heterozygous mice. These data demonstrate that RO7034067 increases SMN protein in both brain and muscle tissues of transgenic mouse models of SMA, and that in the severe SMNΔ7 mouse model, an increase in SMN protein of more than 100% is possible.

EXAMPLE 3

The test item was administered orally by gavage. The animals were dosed over a period of 39 weeks, including the day of necropsy. Animals were not dosed on days of sdOCT evaluation. The Group 4 animals (administered 7.5 mg/kg/day) were not dosed on Days 13 to 25 due to test item-related clinical signs. One female administered 7.5 mg/kg/day (Animal 0114) was not dosed on Day 12 due to its poor clinical condition. The recovery animals were not dosed beyond Day 273 (Week 39).

Study Design and Dose Levels

The following study design and dose levels were selected:

| Group number | Group description | Dose level (mg/kg/day) | Animal numbers Main group | | Recovery group (treatment-free) | |
|---|---|---|---|---|---|---|
| | | | Male | Female | Male | Female |
| 1 | Control | 0 | 3 | 3 | 2 | 2 |
| 2 | Low | 1.5 | 3 | 3 | — | — |
| 3 | Intermediate | 3.0 | 3 | 3 | — | — |
| 4 | High | 75/5[#] | 3 | 3 | 2 | 2 |

[#]Animals were administered 7.5 mg/kg/day on Days 1 to 12. Following a respite period over Days 13 to 25, dosing resumed at 5 mg/kg/day from Day 26 onwards. 5.5 DOSE VOLUME A dose volume of 5 mL/kg was used. Individual dose volumes were based on individual body weights.

Test Item Formulation

Preparation

Formulations were prepared weekly.

The test item was formulated as a solution in 10 mM ascorbic acid/0.0064 mg/mL sodium thiosulfate at pH 3.

Storage

The formulations were stored at 2 to 8° C. with absence of oxygen (under nitrogen), protected from the light in a sealed container. They were allowed to reach room temperature prior to dosing and were stirred on arrival at the animal room and then continuously throughout dosing.

Formulations Analysis

Formulations were analyzed for their test item content.

Stability

Stability data demonstrated formulations in the range 0.025 to 5 mg/mL were stable for up to 4 weeks, when stored at 2 to 8° C. in the absence of oxygen (i.e., under nitrogen).

Achieved Concentration

Samples (3×1 mL aliquots from test item formulations; 2×1 mL aliquots from control item formulations) prepared for use during Weeks 1, 13, 26 and 39, and on Days 12 and 26 of the dosing phase (to coincide with the cessation and restart of dosing for Group 4), were taken for analysis of achieved concentration. The mean of the homogeneity results was taken as the achieved concentration where the sampling occasion coincided.

No samples were taken from formulations prepared for use during Week 9, and samples were collected during Week 13 of the dosing phase.

Test System

Species, Strain and Supplier

Thirty two purpose-bred cynomolgus monkeys (*Macaca fascicularis*) were obtained from Noveprim Ltd (Mauritius) in order to provide 16 healthy animals of each sex.

Specification

Animals were between 24 and 26 months old at the start of dosing.

Environment

Animals were kept in the following environment, except for short periods of time where experimental procedures dictated otherwise. They were housed in exclusive rooms, air conditioned to provide a minimum of 15 air changes/hour. The temperature and relative humidity ranges were generally maintained in the specified ranges of 21 to 25° C. and 40 to 70%, respectively. Fluorescent lighting was controlled automatically to give a cycle of 12 hours light (0600 h to 1800 h) and 12 hours dark.

Animals were housed in pens that conformed to the Code of practice for the housing and care of animals bred, supplied or used for scientific purposes (Home Office, London, 2014). Animals of the same group and sex were group-housed in the same pen.

Diet, Water and Bedding

Each animal was offered pellets of certified lab diet for primates (LabDiet 5048) at least twice daily (approximately six pellets in the morning and six pellets in the afternoon); additional pellets were occasionally offered at the p.m. health checks. Fresh fruit or vegetables were also provided once daily on weekdays, with a dried alternative offered on other occasions.

Mains water was provided ad libitum via water bottles. The water is periodically analyzed for specific contaminants.

Bedding was provided on a weekly basis to each cage by the use of clean Aspen wood chips (Datesand Ltd, Manchester, UK) and Lignocel mix (International Product Supplies Ltd, London, UK).

Dietary Supplements and Environmental Enrichment

The following were offered as a reward: grapes, blueberries, sunflower seeds, pasta, nuts, wood wool and forage mix; these did not require analyses as a form of environmental enrichment.

A number of additional items/strategies were used to enrich the environment and the welfare of animals, such as the provision of toys (balls, inert nylon chews), swings and foraging materials.

Pre-Experimental Procedures

Identification of the Test System

Animals were individually identified by electronic implant.

| Group number | Group description | Dose level (mg/kg/day) | Animal numbers Main group Male | Animal numbers Main group Female | Recovery group (treatment-free) Male | Recovery group (treatment-free) Female |
|---|---|---|---|---|---|---|
| 1 | Control | 0 | 1-3 | 101-103 | 4-5 | 104-105 |
| 2 | Low | 1.5 | 6-8 | 106-108 | — | — |
| 3 | Intermediate | 3.0 | 9-11 | 109-111 | — | — |
| 4 | High | 7.5/5[#] | 13, 15, 16 | 112, 113, 116 | 12, 14 | 114, 115 |

[#]Animals were administered 7.5 mg/kg/day on Days 1 to 12. Following a respite period over Days 13 to 25, dosing resumed at 5 mg/kg/day from Day 26 onwards.

Ophthalmic Examinations
Standard Ophthalmic Examination

Investigations were performed on all animals prior to the initiation of dosing and during Weeks 4, 13, 23 and 36 of the dosing phase.

The investigations during Weeks 23 and 36 were contrary to the Protocol, which specified Weeks 22 and 35 of the dosing phase. The time differences were minimal and had no impact on study integrity.

Animals were lightly sedated with ketamine, and a mydriatic agent was instilled into the eyes prior to indirect and slit-lamp ophthalmic examinations.

Electroretinography (ERG)

Investigations were performed on all animals during Weeks 20, 26 and 34 of the dosing phase and on all recovery animals during Weeks 8, 13 and 22 of the recovery phase.

Animals were fasted for at least 2 hours prior to ERG procedures, dark adapted for at least 2 hours before the scotopic tests, and light adapted for at least 10 minutes before the photopic tests.

Animals were lightly sedated with ketamine, and a mydriatic agent was instilled into the eyes prior to examination.

Spectral Domain Optical Coherence Tomography

Spectral domain optical coherence tomography (sdOCT) was performed on all animals during Weeks 22, 27 and 35 of the dosing phase and Weeks 8, 13 and 22 of the recovery phase.

Animals were fasted overnight prior to examinations and were not dosed on days of sdOCT evaluation.

Animals were lightly sedated with ketamine, and a mydriatic agent was instilled into the eyes prior to examination.

Toxicokinetics

Blood samples for toxicokinetics (nominally 0.5 mL) were taken from all test article-treated animals on Days 1, 12 (Week 2), 26 (Group 4 only), 57 (Week 9), 92 (Week 14), 180 (Week 26) and 267 (Week 39) of the dosing phase at the following time points:

0 (predose), 1, 3, 7 and 24 hours postdose

An additional sample was taken at 72 hours postdose on Day 12 (i.e. Day 15) from all Group 4 animals.

Samples from the control group (Group 1) were taken on different days (except during Week 26) to avoid contamination: Days 3, 15 (Week 3), 59 (Week 9), 89 (Week 13), 180 (Week 26) and 269 (Week 39) of the dosing phase.

On Day 180 of the dosing phase (Week 26), the 1-hour sample from one female (Animal 0111) administered 3 mg/kg/day was taken 6 minutes early, which was 2 minutes outside of the deviation window permitted by SOP. No impact on study integrity occurred as this time deviation was minimal.

Samples were taken from the femoral vein/artery. Each blood sample was mixed gently by hand then placed on crushed wet ice until centrifugation at 2300 g for 10 minutes at approximately 4° C. The resultant plasma was separated, split into two uniquely labelled clear polypropylene tubes and frozen at <−50° C. (nominally −80° C.). One sample was transported frozen on dry ice to the Principal Investigator for analysis, and the other was retained at Covance.

Methods and results are presented in Appendix 13 and Appendix 17.

Clinical Pathology
Samples and Occasions

Blood samples (nominally 0.5 mL collected into EDTA anticoagulant, 0.5 mL collected into trisodium citrate anticoagulant and 0.6 mL collected into lithium heparin anticoagulant) were withdrawn from the femoral vein/artery of all animals prior to the initiation of dosing; during Weeks 4, 13, 26, 35 and 39 of the dosing phase; and during Weeks 13 and 22 of the recovery phase. Samples were collected after an overnight period without food, with the exception of the Week 13 recovery phase samples, for which animals were not starved overnight in error. This was without impact.

Terminal Procedures

All animals were subject to necropsy.

Toxicokinetic Tissue Sampling

The eye—Samples were taken at necropsy for toxicokinteic investigation from the left eye of vitreous and aqueous humor from one animal/sex/group were aliquoted into labelled Eppendorf tubes and weighed. Following excision, the retina, choroid and RPE, cornea, iris, sclera and lens were each placed into separate Precellys homogenization tubes (2 mL: The tubes were then snap frozen in liquid nitrogen and stored frozen at nominal −70° C.

Electron Microscopy

The left eye from two animals/sex/group at the main group necropsy and from one animal/sex/group at the recovery necropsy was fixed in a formalin/glutaraldehyde mixture at necropsy. Using a syringe with a small (25 to 27 gauge) needle, the top of the eye was injected with a 1:1 mixture of 4% buffered glutaraldehyde and 10% NBF into the vitreous body, through the sclera at a location perpendicular to the long posterior ciliary artery. The eye was injected with approximately 0.2 to 0.3 mL of fixative, then submerged in a container filled with 1:1 mixture of 4% buffered glutaraldehyde and 10% NBF for 36 to 48 hours.

Data Evaluation

The number of animals listed in the heading of the summary tables reflects the number of animals assigned to each group at the start of each respective phase, with the exception of the pathology tables, which indicate the number of animals assigned to each respective necropsy interval. The summary table for observations indicates the number of animals for which a condition was observed without regard to the specific nature, severity, reversibility, number of incidences/animal, or the length of time the condition persisted.

Data from test article-treated animals were compared with control data.

Some tables in this report are computer-generated. In this system, individual and derived figures are rounded. Thereby recalculation of derived values from the individual data presented in the reports will, in some instances, yield minor variations.

Statistical analysis was performed on ERG data.

The A wave (where applicable) and B wave amplitude and latency for the electroretinography parameters listed in the following were analyzed using Analysis of Variance (ANOVA; Winer et al., 1991), with treatment as the single factor in the model. If a significant overall treatment effect (P<0.05) was noted, group comparisons (Groups 2, 3 and 4 versus Group 1) were evaluated by Dunnett's-test (Dunnett, 1955 and 1964). Male and female data were analyzed separately.

Scotopic −34 dB Blue Single Flash
Scotopic −8 dB Red Single Flash
Scotopic 0 dB White Single Flash
Oscillatory Potentials
Photopic 0 dB Single Flash
Photopic 0 dB 30.3 Hz White
VEP 4.1 Hz In addition, Levene's test (Levene, 1960) was used to test for equality of variances among groups. Where Levene's test was significant (P<0.01), rank-transformed data (Draper and Hunter, 1969) was used in the ANOVA model.

The average between the two eyes of each animal (right and left) was calculated and used in the analysis.

Results
Formulations

The measured content of all test item formulations ranged between 94 and 103% of nominal, demonstrating acceptable concentrations were prepared for dosing.

Test item was not detected in control samples.

Bioanalysis and Toxicokinetics

The results in plasma indicated the following:

None of the samples from the control group contained quantifiable plasma concentrations of RO7034067. All results were below the lower limit of quantification (<5.00 ng/mL).

All animals administered 1.5, 3 or 7.5/0.5 mg/kg/day were exposed to RO7034067, with complete plasma concentration-time profiles over the whole sampling interval (24 hours) on all investigation days.

Reflux immediately postdose was observed, especially in the group administered 7.5/0.5 mg/kg/day and with high frequency in two animals of this group (Animals 0112 and 0114; not on a toxicokinetic [TK] sampling day for Animal 0112). After 3 days of reflux on Days 89, 90 and 91, the exposure to RO7034067 on Day 92 in Animal 0114 was clearly lower compared with all other animals administered 5 mg/kg/day. This was less pronounced on Day 57 (TK sampling day), when reflux was also observed for this animal. Consequently, the exposure in Animal 0114 was excluded from any ratio and statistics calculations on Days 57 and 92.

Overall, a roughly dose-proportional increase in $AUC_{(0-24h)}$ was observed between 1.5 and 5 mg/kg/day on each evaluation day. This was also observed between 1.5 and 7.5 mg/kg/day on Days 1 and 12.

Overall, no relevant gender differences were observed for $AUC_{(0-24h)}$ or $C_{max}$ at any dose level during the 39-week dosing phase.

The main results (mean values) on Days 12 and 267 are summarized in the following table:

| Occasion | Dose (mg/kg/day) | $C_{max}$ (ng/mL) M/F | $AUC_{(0-24\ h)}$ ((ng · h)/mL) M/F |
|---|---|---|---|
| Day 12 | 7.5 | 1020/1070 | 11200/10200 |
| Day 267 | 1.5 | 414/396 | 1870/2060 |
|  | 3 | 1000/973 | 4880/4850 |
|  | 5 | 701/1160 | 5880/6470 |

AUC = Area under the matrix concentration-time curve from 0 to 24 hours postdose;
$C_{max}$ = Maximum observed concentration;
F = Female;
M = Male.
Note:
Group 4: A dose of 7.5 mg/kg/day was administered from Days 1 to 12; no dose was administered from Days 13 to 25, and a dose of 5 mg/kg/day was administered from Day 26 onwards. Day 267 corresponds to Day 242 for animals administered 5 mg/kg/day (Group 4).

Electroretinography (Non-GLP)
Qualitative Evaluation

Visual inspection of the electroretinography (ERG) responses elicited under the International Society for Clinical Electrophysiology of Vision (ISCEV) Protocol noted several animals administered 7.5/5 mg/kg/day with markedly depressed ERGs during Week 20 of the dosing. One male administered 3 mg/kg/day (Animal 0009) and two males administered 7.5/5 mg/kg/day (Animals. 0013 and 0014) were noted with depressed Scotopic −34 dB Blue B-wave amplitudes. Two females administered 3 mg/kg/day (Animals 0110 and 0111) and three females administered 7.5/5 mg/kg/day (Animals 0114, 0115, and 0116) were also noted with markedly depressed B-wave amplitudes in the Scotopic −34 dB Blue condition. One male (Animal 0014) and two females administered 7.5/5 mg/kg/day (Animals 0114 and 0115) were also noted with reduced Photopic 0 dB White and 30 Hz flicker amplitudes during Week 20 of the dosing phase.

Qualitative evaluation of the ERG responses during Week 26 of the dosing phase indicated depressed Scotopic −34 dB Blue B-wave amplitudes in two males administered 7.5/5 mg/kg/day (Animals 0013 and 0014) and there was in addition evidence of photopic involvement with depressed Photopic 0 dB Single White B-wave amplitudes in two females administered 7.5/5 mg/kg/day (Animals 0114 and 0115).

Qualitative evaluation of the ERG responses during Week 34 of the dosing phase indicated depressed Scotopic −34 dB Blue B-wave amplitudes at 7.5/5 mg/kg/day in three males (Animals 0012, 0014 and 0015) and four females (Animals 0113, 0114 0115, and 0116). One female administered 7.5/5 mg/kg/day (Animal 0114) was noted with a nearly extinguished scotopic and photopic response. One male administered 1.5 mg/kg/day (Animal 0004) had a lower than expected Scotopic −34 dB B-wave amplitude during the Week 34 time point.

Electroretinography (ERG) and VEPs were recorded during Weeks 8, 13 and 22 of the recovery phase in two males and females, from both the control and 7.5/5 mg/kg/day groups. The ERGs recorded from the four control animals were all within the expected normal limits at the three recovery time points. One female previously administered 7.5/5 mg/kg/day (Animal 0114) continued to have a reduced amplitude ERG response during Weeks 8 and 13 of the recovery phase; however, at Week 22 of the recovery phase the amplitude of the ERG B-wave for this animal was noticeably increased compared with the previous tests, although it remained just below the expected normal limits. The two male Group 4 animals had scotopic and photopic B-waves that were within expected normal limits at each of the three recovery intervals Electroretinography Grading The ERG grading was performed semi-quantitatively by comparing the −34 dB Scotopic Blue B-wave amplitude of each animal with values obtained from a large sample (N=320) of cynomolgus monkeys tested with an identical apparatus and anaesthesia (Ver Hoeve et al., 2014). The large sample yield from that study was used to compute lower confidence intervals based on a 1.96*standard deviation and a 2.36*standard deviation, for which the mean was 187.8 and the standard deviation was 51.7 microvolts, corresponding to departures with less than 0.05 or 0.01 probability, respectively. Based on these values, a grading of 0 was assigned to B-wave amplitudes within 1.96 standard deviations; a grading of 1 was assigned to B-wave amplitudes of lower than 1.96 standard deviations below the expected mean but higher than or equal to 2.36*standard deviations, and a grading of 2 assigned to B-wave amplitudes below 2.36 standard deviations from the expected mean.

Dosing Phase

Based on grading criteria previously described, 4 of 5 females administered 7.5/5 mg/kg/day had depressed rod responses during Week 20; 2 of 5 females administered 7.5/5 mg/kg/day had depressed rod responses during Week 26; and 4 of 5 females administered 7.5/5 mg/kg/day had depressed rod responses during Week 34 of the dosing phase. Four of five males administered 7.5/5 mg/kg/day had depressed rod responses during Week 20; 2 of 5 males administered 7.5/5 mg/kg/day had depressed rod responses during Week 26; and 5 of 5 males administered 7.5/5 mg/kg/day had depressed rod responses during Week 34 of the dosing phase.

Using these grading criteria, all three females administered 3 mg/kg/day had depressed rod responses during Week 22; none of these females had depressed rod responses during Week 27; and 1 of 3 females administered 3 mg/kg/day had depressed rod responses during Week 35 of the dosing phase. For males administered 3 mg/kg/day, 1 of 3 had depressed rod responses during Week 22, while none did during Week 26 or 35 of the dosing phase.

Two females administered 1 mg/kg/day had rod ERGs that were below the criteria during Week 34 of the dosing phase. No males administered 1 mg/kg/day had a rod response that was below the expected range.

Amongst control animals, only one female (Animal 0102) had rod responses outside the expected range, occurring during Weeks 22 and 34 of the dosing phase. Only one control male had a rod response below the criterion, occurring during Week 34 of the dosing phase.

The OCT and ERG findings were sparse or absent in control and the group administered 1 mg/kg/day. The OCT and ERG found relatively mild abnormalities in animals administered 3 mg/kg/day, and both indicated a high percentage of abnormalities were present in animals administered 7.5/5 mg/kg/day.

Recovery Period

Two control animals/sex and two animals/sex administered 7.5/5 mg/kg/day were followed during recovery and tested during Weeks 8, 13, and 22 of the recovery phase.

One of the two females given 7.5/5 mg/kg/day during the dosing phase, with significantly reduced rod responses at Weeks 22, 26, and 34 of the dosing phase (Animal 0114) remained depressed at Recovery Week 8 and Recovery Week 13. At Recovery Week 22, No. 114 showed a large increase in B-wave amplitude, from 34.1, 33.5 (mcV, right, left eye) at recovery week 8 to 43.4, 52.7 mcV at recovery Week 22. However, this response remained more than 2.36 standard deviations below expected mean. The other affected Group 4 female, No. 0115, had ERG B-waves that were less affected yet below expected limits at Recovery Week 8 and 13 with full recovery at Week 22 of the Recovery period. Both Group 4 males had scotopic and photopic b-waves that were within the expected normal limits at each of the three recovery tests.

Quantitative Evaluation

Statistical evaluation of the ERG A- and B-wave peak latencies (implicit time) and amplitudes from data collected during Week 34 of the dosing phase was performed by Covance statisticians.

Scotopic −34 dB Blue Single Flash B-wave amplitude was significantly different between groups ($P<0.0047$), as was B-wave latency ($P<0.0370$), although individual group comparisons with control (Dunnett's test) did not reach significance with this small N analysis.

The latency of the Scotopic 0 dB White A-wave differed significantly between groups ($P<0.0116$), with Dunnett's test significant for the difference between the 7.5/5 mg/kg/day group and the control group ($P<0.0095$).

Finally, the Photopic 0 dB White B-wave amplitude differed significantly among groups ($P<0.0449$), although group comparisons with control failed to reach significance.

In summary, several animals administered 7.5/5 mg/kg/day were noted with markedly depressed scotopic and photopic ERGs during Week 20 of the dosing phase. Retinal function remained depressed in these animals during Week 26 and 34 of the dosing phase, with one female administered 7.5/5 mg/kg/day (Animal 0114) clearly showing signs of progressive ERG dysfunction. Of note, No. 0114 showed definite signs of recovery by Week 22 of the recovery phase. Intermediate and low dose group animals (3.0 and 1.5 mg/kg/day) generally remained within expected limits with no evidence for a trend toward reduced ERG amplitudes during the dosing phase.

In affected animals, a marked depression of the rod photoreceptor-mediated Scotopic—34 dB Blue Single flash was noted. In the most affected animals (three males [Animals 0012, 0014, and 0015] and two females [Animal 0114 and 0116] administered 7.5/5 mg/kg/day), the Scotopic 0 dB Single White (mixed rod-cone stimulus) A-wave appeared less depressed than the B wave. This suggested RO7034067 had a relatively greater effect on photoreceptor to bipolar cell transmission than on photoreceptor activation per se. This reasoning lead to the possibility that the bipolar cell layer was a primary locus of retinal dysfunction in animals administered 7.5/5 mg/kg/day.

It was also notable that marked individual differences were noted in response to administration of RO7034067, with some animals administered 7.5/5 mg/kg/day exhibiting normal ERGs and others, noted previously, with depressed ERGs. The flash-evoked VEP remained present even in animals administered 7.5/5 mg/kg/day. This suggested RO7034067 administration did not significantly compromise retinal ganglion cells or their axonal projections to the visual cortex, even in animals with affected retinal responses. This could occur if the macular region was relatively spared compared with peripheral retinal, which occupies a much larger proportion of the retina and is largely responsible for the full-field ERG. By sdOCT and with histopathology, it was shown that, indeed, the macula region was spared from any substantial retinal damage.

No animals administered 1.5 mg/kg/day or control item (vehicle) were noted with ERG deficits.

Spectral Domain Optical Coherence Tomography (sdOCT, Non-GLP)

Dosing Phase

Three males administered 7.5/5 mg/kg/day (Animals 0012, 0014 and 0016) appeared to be slightly worse during Week 27 compared with Week 22. Animal 0014 had an increase in microcystoid macular degeneration (MMD) and fluid spaces in the ONL in the periphery, while Animal 0016 had more thinning and disorganization in the periphery. The MMD spaces were only noted in the INL and were distinct in appearance from the spaces noted in the ONL in the periphery. During Week 35, Animal 0014 also appeared slightly worse than during Week 27, with a continued increase in the number of MMD and fluid spaces in the INL and ONL in the periphery and slightly increased thinning and disorganization of retinal layers in the periphery.

During Week 27, one female administered 7.5/5 mg/kg/day (Animal 0113) had fewer MMD spaces near the optic nerve head and macula than during Week 22 but more disorganization of the retinal layers in the periphery; one female administered 7.5/5 mg/kg/day (Animal 0114) had more MMD, with cystoid spaces in the INL extending into the periphery, and slightly more disorganization and thinning in the periphery than during Week 22; one female administered 7.5/5 mg/kg/day (Animal 0116) had spaces in the INL in the periphery and near the optic nerve. During Week 35, one female administered 7.5/5 mg/kg/day (Animal 0113) still had MMD spaces near the optic nerve head and macula; however, more disorganization of the retinal layers were noted in the periphery than during Week 27, with optically empty spaces noted under the ILM (in the left eye more so than the right); Animal 0114 had more MMD during Week 35 than during Week 27, with cystoid spaces in the INL extending into the periphery, more disorganization and thinning in the periphery, and an increase in optically empty spaces in the ONL and under the LM. Also during Week 35, Animal 0115 had an increase in MMD spaces in the INL extending into the periphery compared to Week 27, as well as rare spaces in the ONL.

Males administered 3 mg/kg/day had minimal/mild retinal disorganization in the periphery throughout the sdOCT intervals (Weeks 22, 27 and 35 of the dosing phase). Two females administered 3 mg/kg/day (Animals 0109 and 0110) appeared slightly worse during Week 27 than during Week 22, with more ONL infiltrates/reflective spots and inner segment/outer segment (IS/OS) dropout. During Week 35, one female administered 3 mg/kg/day (Animal 0109) showed a larger area, where the IS/OS was absent in the periphery.

Control and animals administered 1.5 mg/kg/day retained a normal retinal appearance.

Fundus autofluorescence (FAF) images showed little change overtime in groups administered control item (vehicle), 1.5 or 3 mg/kg/day. Mottled hypofluorescence was only noted in the most affected animals administered 7.5/5 mg/kg/day. These dark punctate spots appeared to coalesce into larger dark patches in the far periphery, where retinal degeneration was most pronounced, in some animals administered 7.5/5 mg/kg/day. A dark ring was noted around the fovea in FAF images of eyes with extensive MMD. This FAF finding has been reported in a number of ophthalmology journal articles documenting MMD in human patients.

Discussion

The prime effect noted in this study was a dose- and incidence-related effect of RO7034067 on retinal integrity and function. ERG and sdOCT were implemented from Week 20 of the dosing phase for subsequent identification of retinal changes in a chronic monkey toxicity study with another test item of similar pharmacological properties. In order to monitor retinal changes during in-life, the dosing phase was extended from 13 to 39 weeks. During treatment with RO7034067, a clear association was noted between animals identified with structural abnormalities on sdOCT and animals identified with functional abnormalities on ERG with more severe abnormalities on sdOCT having been associated with depressed ERG wave responses. The association was present at the first investigation during Week 20/22 of the dosing phase and persisted at the two following investigations during the dosing phase. Some animals with only slight abnormalities in sdOCT in the 3 mg/kg/day dose group did not display any functional changes by ERG. In addition, three animals administered 7.5/5 mg/kg/day (Animals 0014, 0114, and 0116) were the most affected animals according to sdOCT grading and had the greatest ERG depression.

FIG. 3 displays the exposure-effect correlation for sdOCT, ERG and histopathological changes with individual animal exposures at the end of the study duration (and at the end of the 22-week recovery phase for histopathology). Animals exposed on average of 1870/2060 ng-h/mL AUC0-24 h in males and females, respectively, and up to 2300 ng-h/mL AUC0-24 h individually, were free of effects on the retina. The lowest exposures of animals at the mid-dose with retina findings were 4540/4560/4560 ng-h/mL AUC0-24 h for animal Nos. 11, 109 and 111. Effects were seen by sdOCT and histology at an exposure of 4880/4850 ng-h/mL (AUC0-24 h in M/F) at a dose of 3 mg/kg/day. Depressed ERG and microcystic spaces in the INL were seen mostly in animals at the high dose (5 mg/kg/day) with an exposure of 5880/6470 ng-h/mL (AUC0-24 h in M/F). Exposures showed only very low variability over time during the study.

The OCT findings in all animals, to some degree, administered ≥3 mg/kg/day included disorganization and thinning of the IS/OS and increased reflectivity and thinning of the ONL in the retinal periphery. Microcystoid macular degeneration (MMD), characterized by a distinctive pattern of microcystoid spaces in the INL, was also noted. What appeared to be fluid accumulation was noted under the ILM and in the ONL. These effects correlated with adverse histopathologic findings of degeneration in the mid to peripheral area of the retina of one female administered 3 mg/kg/day and two animals/sex administered 7.5/5 mg/kg/day and were characterized by multifocal disorganization of the outer nuclear and photoreceptor layers of the retina, with some loss of photoreceptor layer; multifocal hypertrophy of retinal pigment epithelial cells; some thinning, disorganization, and vacuolation of the inner nuclear layer; and vacuolation of the ganglion cell layer.

Microcystoid macular degeneration (MMD) is a distinct finding from fluid spaces under the ILM and in the ONL; MMD, as often reported in the literature as microcystoid macular edema, is usually associated with degenerative diseases, such as MS or glaucoma. Its etiology is poorly understood, but the normal presentation is of a distinctive pattern of microcystoid spaces in the parafoveal region, occasionally extending farther out in the periphery, but always in the INL and always with a long narrow and vertical appearance to the spaces versus the varied appearance of fluid spaces in the ONL or under the ILM, which are irregular in shape and may be wider than they are tall. The thinned nature of the INL in the far periphery made it difficult to appreciate the exact shape of the space; some looked like classic MMD and appeared to be extensions of the spaces noted around the macula, but other spaces in the INL in the periphery did not.

In the far periphery of the retina, some thinning of the ONL and some disorganization of the photoreceptor/RPE layers is normal. Image quality is degrading towards the far periphery, especially in monkeys, in part due to their smaller eyes and increased curvature, so definitive conclusions about retinal layer integrity were more difficult in that location. When comparing images across groups, however, there appeared to be a dose response on sdOCT, with higher dose groups showing more disorganization and thinning in the IS/OS and more accumulations of fluid in the ONL and INL and under the ILM in the periphery and MMD spaces around the macula. Also, females administered 3 or 7.5/5 mg/kg/day appeared more affected than males in these groups.

Fundus autofluorescence (FAF) imaging showed areas of speckled hypofluorescence and hyperfluorescence solely in the periphery of animals with the most pronounced degenerative changes; FAF is used to record fluorescence that may occur naturally in the eye or accumulate as a byproduct of a disease process and can provide useful information on conditions where the health of the RPE plays a key role. Hyper-autofluorescence may be a sign of increased lipofuscin accumulation, which may indicate degenerative changes or oxidative injury. Areas of hypo-autofluorescence may indicate missing or altered RPE cells. The FAF changes in the current study pointed to degenerative changes in the peripheral retina and MMD around the fovea.

The bright, speckled areas of hyper AF signal, noted in the far periphery, may have originated from increased lipofuscin formation in degenerating photoreceptor cells impaired by the failure of RPE. In general, hypo AF (dark) areas indicate missing or altered RPE cells and are where the most degenerative changes—photoreceptor loss and ONL disorganization—were noted. Over time, hyper AF areas that suggest sick RPE cells can become zones of hypo AF, suggesting loss of RPE. The band of white hyper AF spots noted in the far periphery of animals administered 7.5/5 mg/kg/day could have been considered a transition zone, where the cells may have impaired function; however, potential for recovery still exists. The fact that the transition zone in the far periphery remained the same early in the recovery phase but appeared to recede by Week 22 of the recovery phase may have indicated the tipping point for irreversible damage was not reached in that area and that, over time recovery, was possible. The OCT findings and ERG testing showed clear improvement in all animals, especially at the last interval, Week 22 of the recovery phase. Only in one animal out of 4, ERG remained below normal limits.

It should be noted that, in FAF imaging, particularly in monkeys, there may be subtle changes in FAF appearance that are due to slight changes in orientation and/or eye movement. The software averages up to 100 frames to create the final image, and that can result in some image contrast or shading variability. The images collected in the far periphery of the most affected animals did show changes that appeared to correlate with the more pronounced degenerative changes. A caveat in the interpretation of the results was that not all animals were imaged at each interval and it was difficult to make definitive statements about FAF appearance, dose response, and progression over time with such a small sample size.

The OCT findings correlated with pathology findings of retinal degeneration, characterized by disorganization of the outer nuclear and photoreceptor layers of the retina, with multifocal loss of the photoreceptor layer in the periphery. The pathology findings of thinning, disorganization, and vacuolation of the inner nuclear layer were consistent with the OCT finding of MMD, and vacuolation of the ganglion cell layer was consistent with the OCT finding of an increase in the optically empty spaces (fluid) under the LM. The OCT finding of MMD in the INL was focal in nature, and the spaces (or vacuoles) would not necessarily be noted on histopathology sections Histopathologically, retinal degeneration was not reversible during the recovery period, although vacuolation of the inner nuclear layer was no longer present. The retinal degeneration was considered to be adverse.

Conclusion

Administration of 1.5, 3 or 7.5/5 mg/kg/day RO7034067 to cynomolgus monkeys for 39 weeks was primarily associated with clinical signs in the skin of animals administered 7.5/5 mg/kg/day, which correlated with nonadverse microscopic findings of epidermal hyperplasia. In addition, dose-related in incidence and severity functional (as measured by ERG) and morphological (adverse retinal degeneration) changes in the eye were observed in animals administered 3 or 7.5/5 mg/kg/day, and the thymus (nonadverse) of females administered 7.5/5 mg/kg/day was also identified as a site of test item-related histopathological change.

Based on the findings in the eye of animals administered 3 or 7.5/5 mg/kg/day and the absence of any test item effects in animals administered 1.5 mg/kg/day, under the conditions of this study, the No Observable Adverse Effect Level (NOAEL) is considered to be 1.5 mg/kg/day, corresponding to systemic RO7034067 exposures of 414/396 ng/mL ($C_{max}$) and 1870/2060 ng hr/mL ($AUC_{0-24}$) during Week 39 of the dosing phase for males/females.

In the monkey 39-week chronic toxicity study (with a 22-week recovery phase), peripheral retinal degeneration (photoreceptor loss), hyper-reflective RPE and more central MMD (vacuoles) were detected by sdOCT (assessed from week 20 of treatment onwards) at an exposure of 4260 ng·h/mL $AUC_{0-24h}$. Complementary acquisition of ERG data showed depressed B-wave It was noted in the retina from the chronic 39-week toxicity study in monkeys that Multifocal peripheral retina degeneration in the photoreceptor layer with hypertrophic RPE and microcystic spaces (vacuoles) in the inner retinal layers in monkeys as detected by sdOCT. This was associated with depressed scotopic (rod) B-wave and somewhat less affected photopic (cone) B-wave in the ERG. sdOCT and ERG evaluation was initiated in week 20 (subsequent to reporting of retinal changes for RO6885247 at the end of the chronic monkey toxicity study with that molecule) and continued until week 35 of the study. These findings were confirmed by histopathology. The NOEL of the retina finding with 39 weeks of treatment is 1870/2060 ng·h/mL ($AUC_{0-24h}$ in M/F) with effects seen by sdOCT and in histology at an exposure of 4880/4850 ng·h/mL ($AUC_{0-24h}$ in M/F). Depressed ERG and microcystic spaces in the INL were only seen in animals at the high dose with an exposure of 5880/6470 ng·h/mL ($AUC_{0-24h}$ in M/F).

Experimental evidence suggests that the effect on the retina is not directly associated with effects on tissue proliferation but related to in vitro evidence of high melanin binding and tissue retention in the retina. Despite high tissue accumulation and tissue retention in monkey and pigmented rat RPE/retina, no evidence for any retinal effects was present after 26 weeks of treatment in pigmented rats at which time retinal changes were clearly seen in monkeys. Thus, melanin-bound RO7034067 does not confer toxicity per se and factors additional to the presence of high levels of melanin-bound RO7034067 must play a role in its retinal effects in monkeys. Impairment of lysosomal function/autophagosomal accumulation was seen in human RPE cells in vitro.

All features of retinal degeneration were confirmed by histopathology and did not appear to impair vision of the animals (based on general behavior and ophthalmology assessments) despite markedly depressed B-waves in a few animals with high exposure. The MMD and depressed ERG almost fully recovered in the 22-week recovery phase of the monkey study but the peripheral photoreceptor loss and hyper-reflective/hypertrophic RPE did not. For RO7034067, no retina changes were seen in 2-week monkey toxicity studies with individual exposures up to 15,100 ng·h/mL $AUC_{0-24h}$. Over the in-life duration of the 39-week monkey toxicity study with RO7034067, the low dose remained free of any test-item related changes in sdOCT and ERG until the last week of assessment (week 35). At this low dose of 1.5 mg/kg/day, the retina was also free of any histopathological changes corresponding to systemic RO7034067 exposures of 414/396 ng/mL ($C_{max}$) and 1870/2060 ng·h/mL ($AUC_{0-24}$) at week 39 for Male/Female, respectively.

EXAMPLE 4

FoxM1, a gene alternatively spliced by other splicing modifier compounds, encodes a cell cycle regulator. Using RT-qPCR with specific primers for FoxM1a (FL), and FoxM1b/c (Δ9), the modification of alternative splicing of FoxM1 after RO7034067 treatment was confirmed ($EC_{50}$ 67±32 nM for FL, 139±43 nM for Δ9 mRNA; see FIG. 4). Increased abundance of the FoxMJA isoform, together with decreased abundance of FoxM1 isoforms lacking exon 9, has the capability to disturb and inhibit cell cycle progression if splicing changes are at a level that is biologically significant. Thus, RO7034067 acts in a similar way on the SMN2 and FoxM1 splicing machinery, but with opposing outcomes with regard to protein function. MADD, a gene involved in apoptosis processes, has also been identified as a secondary splice target.

The functional consequences of dysregulation of FoxM1 and MADD identified in toxicological studies with RO7034067 (including cell cycle analysis and RNA sequencing investigations in animal tissue) are described below.

In vitro studies that were conducted with a series of SMN2 splicing modifiers, which included RO7034067, suggested that a distinct number of gene transcripts could be affected by alternative splicing (Palacino J. et al. Nat Chem Biol. 2015; 11:511-7). Hence, to enhance mechanistic understanding of toxicities provoked by treatment with RO7034067, RNA-sequencing analysis followed by detailed analysis of spliced genes were integrated into the 2-week dose-range finding repeat dose toxicity studies conducted in the rat and monkey for RO7030467. Gene expression analysis was performed in spleen, duodenum, and testis in rats treated for 2 weeks (MADD gene). Gene expression analysis of R7034067-treated animals revealed a splicing response at the highest dose of 7.5 mg/kg/day for MADD gene transcripts and in spleen, duodenum, and testis. The changes in splicing of MADD transcripts are consistent with the observations of apoptosis in the GI tract observed at the same dose since MADD gene products have been reported to interfere with the apoptosis processes.

Similar investigations were integrated into the 2-week dose-range finding toxicity study conducted in the cynomolgus monkey with RO7034067. For this purpose, spleen, duodenum, and testis were analyzed from the animals treated with 0.75, 1.5, 3 and 6 mg/kg/day. The analysis with mRNA isoform specific qPCR assays revealed a secondary pharmacological response to RO7034067 treatment at the highest dose for the transcripts of the MADD gene transcript in all three organs. Since secondary pharmacology was detected in spleen, this organ was further analyzed for transcriptome-wide mRNA splicing or expression changes by RNA-sequencing. This analysis revealed that, apart from the above-mentioned spliced transcripts, the vast majority of mRNAs exhibited either no change in alternative splicing or no dose-dependent trend with respect to changes in alternative splicing upon treatment with RO7034067. Furthermore, a dose-dependent trend for pathway expression changes was not detected. Therefore, while the few changes in R7034067-mediated alternative transcript splicing are consistent with in vitro data and those of other SMN2 splicing modifiers, they seem not to fundamentally affect biological pathways or processes under the conditions of this study.

EXAMPLE 5

Test and Control Items

| Test Items | | |
|---|---|---|
| Compound | Molecular Weight | Stock Solution |
| RO7034067 | MW 401.26 | 1250 μM in DMSO |

Control Items
Rapamycin, Sigma-Aldrich #R8781, 2.5 mg/ml (2.74 mM) stock solution 2 mM in DMSO, diluted in DMSO to 3.75 μM and stored in aliquots at −20° C.

Culture of Induced Pluripotent Stem Cells

Human iPSCs (hIPS_Neo_Clone_1) were cultivated in mTeSR1 (Stem Cell Technologies) as standard medium and Cynomolgus monkey iPSCs (cips_54-1285_cFIB_Clone_8) in MT medium supplemented with 10 ng/ml ActivinA and 15 ng/ml FGF2.

For gene expression profiling, stem cells were detached with Accutase (Stem Cell Technologies) and plated in 12 well plates coated with Matrigel (BD Biosciences) in the respective standard medium supplemented with 10 μM Rock inhibitor Y-27632 (Sigma-Aldrich). In order to obtain enough RNA, monkey stem cells were seeded at 15000 cells/cm2 and human stem cells were seeded at 40000 cells/cm2 24 h prior to treatment. Thereafter stem cells were treated for 24 h with serial dilutions (1:5) of test items in fresh, pre-warmed medium in a concentration range from 0.64 nM till ~10 μM. To stop the experiment, cells were lysed in QiaGen's lysis buffer RLT with beta-mercaptoethanol.

For the analysis of the cell cycle, monkey stem cells were detached with Accutase (Stem Cell Technologies) and plated at 15000 cells/cm2 in 6 well plates coated with Matrigel (BD Biosciences) in MT medium supplemented with 10 ng/ml ActivinA, 15 ng/ml FGF2, and 10 μM Rock inhibitor. Cells were expanded for 1 day and then synchronized by starvation for 7 h in MT medium without supplements FGF2 and ActivinA. Before flow cytometry, cells were incubated for 24 h with fresh MT medium containing supplements FGF2 and ActivinA and test items at 80 nM, 400 nM, and 2000 nM or 30 nM rapamycin as positive control to arrest cells in G1 phase. Human stem cells were detached with Accutase (Stem Cell Technologies) and plated at 40000 cells/cm2 in 6 well plates coated with Matrigel (BD Biosciences) in mTeSR1 supplemented with 10 µM Rock Inhibitor Y-27632 (Sigma-Aldrich). Cells were expanded for 3 days with daily medium change. Since human iPSCs lose their properties during starvation by growth factor withdrawal, stem cells were synchronized with 200 ng/ml Nocodazole (Sigma-Aldrich) for 5 h and washed subsequently 2 times with mTesR1 Medium. Before flow cytometry, cells were incubated for 24 h with fresh TesR1 medium containing test items at 80 nM, 400 nM, and 2000 nM or 30 nM rapamycin as positive control to arrest cells in G1 phase.

Flow Cytometry and DNA Staining

For cell cycle analysis, human iPSCs were washed with PBS, detached with Accutase (Stem Cell Technologies) and collected by centrifugation. Cells were stained for 1 h at 37° C. with 600 ul of 7AAD/Saponin/RNAse mix (25 µg/ml 7AAD (#559925, BD), 50 µg/ml RNase, and 0.03% Saponin dissolved in FACS buffer (PBS, 5% FBS, 10 mM Hepes)). Cynomolgus monkey iPSCs were washed with PBS, detached with Accutase (Stem Cell Technologies) and collected by centrifugation. Cells were stained for 30 min at 37° C. in 300 ul standard MT medium (with FGF2 and ActivinA) containing 1 ul Vybrant Dye Cycle Violet Stain (#V35003, 1000× stock, Invitrogen) per ml medium. Additionally 2 ul 7AAD (50 µg/ml 7AAD) were added without permeabilization to label dead cells; cells were incubated for 10 min at 37° C. Flow cytometry analysis was performed using a Canto II cytometer (BD Biosciences) and data were analysed with the FlowJo software.

Quantitative Real Time PCR

Human and Cynomolgus monkey mRNA expression was measured with customized primer and FAM fluorescently-labeled Universal Probe Library (UPL) probes from Roche or probes from Microsynth containing a 5' FAM label and a 3' terminal BlackHole Dark Quencher 1 (BHQ1). The sequences of the primer and FAM labeled probes are listed as follows:

protocol. The quantitative PCR was performed on a Light-Cycler 480 qPCR machine using 67.5 ng total RNA derived cDNA as input in a 20 µl mixture containing 1× LightCycler 480 Probes Master, 0.4 µM forward and reverse primers, and 0.2 µM FAM labeled hydrolysis probe. The temperature program consisted of pre-incubation at 95° C. for 10 min, followed by 50 cycles of amplification (95° C. for 10 s, 60° C. for 30 s, 72° C. for 5 s). Negative control reactions were conducted in the absence of cDNA template to confirm absence of cDNA contamination in the master mix. Measurements of Ct (cycle threshold)-values were performed for each sample-mRNA combination. Using the 2-ΔΔCt method (Livak K J et al. Method. Methods. 2001; 25(4):402-8), the data are presented as the fold change in gene expression normalized to an endogenous reference gene and relative to the untreated control. To derive individual ΔCt values, the Ct value for each target mRNA of each sample was normalized to the Ct value of the endogenous reference mRNA of GAPDH (glyceraldehyde-3-phosphate dehydrogenase). The ΔCt value was calculated by subtracting the ΔCt value of the vehicle-control group from the respective ΔCt value of each treatment group. Resultant expression ratios (2-ΔΔCt) mirrored treatment-related mRNA expression changes versus vehicle-controls. The IC50 is defined as the concentration of inhibitor that provokes a response half way between the maximal (Top) response and the maximally inhibited (Bottom) response. The model to derive the IC50 assumes that the dose response curves has a standard slope, equal to a Hill slope (or slope factor) of −1.0. Model equation: Y=Bottom+ (Top-Bottom)/(1+10^((X-LogIC50))); with Y being the response data and X being log 10 concentrations in µM.

Results

RO7034067 was tested in vitro for their concentration-effect relation on the expression of FOXM1 mRNA variants (FOXM1B/C). Expression levels of FOXM1B/C transcript variants were measured relative to GAPDH by RT-qPCR in human and monkey iPSCs treated with the test items for 24 h from 0.64 nM till ~10 µM. Treatment with RO7034067

| target mRNA | primer/probe | | sequence (5' -> 3') | SEQ ID NO |
|---|---|---|---|---|
| FOXM1B/C# | forward primer | (exon 8/10) | CCCCCAAGGTGCTGCTA | 1 |
| | reverse primer | (exon 10) | TGAACTGGAAGCAAAGGAGAA | 2 |
| | FAM-BHQ1 | (exon 10) | CTTTCTTCTGCAGGACCAGG | 3 |
| GAPDH*,# | forward primer | | GAAGGTGAAGGTCGGAGTCA | 4 |
| | reverse primer | | AACCATGTAGTTGAGGTCAATGAA | 5 |
| | FAM-UPL 147 | | TTGATGGC | 6 |
| FOXM1B/C* | forward primer | (exon 8/10) | CCCCCAAGGTGCTGCTA reverse | 7 |
| | reverse primer | (exon 10) | TGAACTGGAAGCAAAGGACAC | 8 |
| | FAM-BHQ1 | (exon 10) | CTTCCTTCTGCAGGGCCAGG | 9 | species specificity of primer/probes: # . . . human; * . . . Cynomolgus monkey

For quantitative Real-Time-PCR, cells cultivated in a 12 well plate and treated with Roche-compounds for 24 h were lysed in 500 ul/well of QiaGen's lysis buffer RLT with beta-mercaptoethanol. Total RNA was extracted with the RNeasy Mini kit combined with DNase treatment on a solid support. RNA integrity was controlled by using Nanodrop absorption spectroscopy and microfluidic capillary array electrophoresis profiles from an Agilent Bioanalyzer 2100. Between 300 ng to 800 ng of total RNA were reverse transcribed with oligo-dT primer and spiked MS2 RNA at 10 ng/uL final concentration using the Transcriptor First Strand cDNA Synthesis Kit (Roche Applied Science #04379012001) following the manufacturer's recommended resulted in a concentration dependent down-regulation of FOXM1B/C transcript variants in human and monkey cells (Table 1 and Table 2). In human and monkey cells RO7034067 was affecting the expression levels of FOXM1B/C, IC50 values were 114 nM and 155 nM in human and monkey cells, respectively (FIG. 5).

RO7034067 was tested in vitro for its concentration-dependent effect on cell cycle of iPSCs. In monkey iPSCs, compound RO7034067 induced a cell cycle arrest in G2 phase in a concentration-dependent way. In human iPSCs, RO7034067 induced cell cycle arrest in S phase in a concentration-dependent way (Table 3 and Table 4). Treatment with 30 nM rapamycin resulted as expected in an arrest of human and monkey cells in G1 phase (Metcalfe et al. Oncogene 15, 1635-1642).

TABLE 1

Relative mRNA expression data on human iPSCs for RO7034067

| concentration nM | Mean FOXM1B/C | SD | SEM |
|---|---|---|---|
| 0 | 1.016 | 0.231 | 0.133 |
| 0.64 | 1.115 | 0.084 | 0.048 |
| 3.2 | 1.032 | 0.094 | 0.054 |
| 16 | 0.898 | 0.023 | 0.013 |
| 80 | 0.748 | 0.073 | 0.042 |
| 400 | 0.178 | 0.017 | 0.010 |
| 2000 | 0.185 | 0.020 | 0.011 |
| 10000 | 0.102 | 0.016 | 0.009 |

Real Time PCR signals were normalized to GAPDH, and mRNA expression ratios ($2^{-\Delta\Delta Ct}$) were calculated for each treated sample relative to the control sample of human iPSCs.

TABLE 2

Relative mRNA expression in Cynomolgus monkey iPSCs

| concentration nM | Mean FOXM1B/C | SD | SEM |
|---|---|---|---|
| 0 | 1.000 | 0.035 | 0.020 |
| 0.64 | 0.967 | 0.097 | 0.056 |
| 3.2 | 0.990 | 0.129 | 0.075 |
| 16 | 0.963 | 0.120 | 0.069 |
| 80 | 0.704 | 0.049 | 0.028 |
| 400 | 0.176 | 0.024 | 0.014 |
| 2000 | 0.023 | 0.001 | 0.001 |
| 10000 | 0.037 | 0.001 | 0.001 |

Real Time PCR signals were normalized to GAPDH, and mRNA expression ratios ($2-\Delta\Delta Ct$) were calculated for each treated sample relative to the control sample of Cynomolgus monkey iPSCs.

TABLE 3

Cell cycle human data: percentage of events in G1, S and G2 phases for the cell cycle

| | mean | | | SD | | | p-value | | |
|---|---|---|---|---|---|---|---|---|---|
| | G1 | S | G2 | G1 | S | G2 | G1 | S | G2 |
| no treatment | 44.7 | 23.9 | 31.4 | 1.9 | 0.3 | 2.2 | | | |
| DMSO | 45.7 | 24.3 | 30.1 | 1.9 | 0.8 | 1.7 | | | |
| RO7034067 80 nM | 44.6 | 26.2 | 29.2 | 1.1 | 1.1 | 2.2 | 4.5E-01 | 7.5E-02 | 6.2E-01 |
| RO7034067 400 nM | 40.8 | 27.8 | 31.4 | 3.8 | 1.5 | 5.3 | 1.4E-01 | 3.5E-02 | 7.1E-01 |
| RO7034067 2000 nM | 37.6 | 33.1 | 29.3 | 1.5 | 1.0 | 1.3 | 5.2E-03 | 3.8E-04 | 5.5E-01 |
| Rapamycin 30 nM | 58.3 | 11.2 | 30.5 | 0.7 | 0.4 | 0.8 | 3.2E-03 | 1.1E-04 | 7.2E-01 |

TABLE 4

Cell cycle Cynomolgus monkey data: percentage of events in G1, S, and G2 phases for the cell cycle

| | mean | | | SD | | | p-value | | |
|---|---|---|---|---|---|---|---|---|---|
| | G1 | S | G2 | G1 | S | G2 | G1 | S | G2 |
| no treatment | 32.1 | 13.4 | 54.5 | 1.4 | 0.5 | 1.8 | | | |
| DMSO | 36.2 | 14.6 | 49.1 | 1.3 | 1.6 | 2.1 | | | |
| RO7034067 80 nM | 33.8 | 14.0 | 52.2 | 2.2 | 0.7 | 2.9 | 1.90E-01 | 5.90E-01 | 2.10E-01 |
| RO7034067 400 nM | 30.3 | 14.0 | 55.8 | 0.8 | 0.3 | 0.7 | 5.20E-03 | 5.60E-01 | 2.30E-02 |
| RO7034067 2000 nM | 25.3 | 13.4 | 61.3 | 0.7 | 0.5 | 0.5 | 1.20E-03 | 3.10E-01 | 7.30E-03 |
| Rapamycin 30 nM | 41.7 | 12.7 | 45.6 | 2.2 | 0.5 | 1.8 | 3.00E-02 | 1.70E-01 | 8.90E-02 |

Conclusion

To assess effects of RO7034067 splicing modifier on and FOXM1 marker mRNA expression and the cell cycle, in vitro testing for concentration-effect relations was conducted with induced pluripotent stem cells from human and Cynomolgus monkeys. Upon treatment with RO7034067 for 24 h from 0.64 nM till ~10 µM the compound showed a concentration dependent down-regulation of FOXM1B/C transcript variants. IC50 values derived from the concentration-response curves were comparable between human and Cynomolgus monkey cells demonstrating high species similarities in pharmacological response. A concentration-dependent effect to induce mitotic arrest in Cynomolgus monkey cells was detected for RO7034067. The cell cycle analysis of human IPSCs revealed a concentration-dependent effect altering the cell cycle with RO7034067. Down-regulation of FOXM1B/C seems to be associated with cell cycle related findings in both human and Cynomolgus monkey cells, which would be consistent with the critical role of FOXM1 in mediating cell cycle transitions. This down-regulation has to be pronounced with a decrease in expression of ~80% or more to be associated with a significant alteration of the cell cycle.

What is claimed is:

1. A method of treating spinal muscular atrophy (SMA) in a subject in need thereof comprising administering to said subject 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof, wherein the administered dose of 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is
   a. 0.25 mg/kg for a subject with a body weight of less than 20 kg, and
   b. 5 mg for a subject with a body weight of more than or equal to 20 kg.

2. The method of claim 1, wherein the SMA is type II SMA.

3. The method of claim 1, wherein the SMA is type III SMA.

4. The method of claim 1, wherein the SMA is type II SMA and type III SMA.

5. The method of claim 1, wherein the subject is more than or equal to 2 years of age.

6. The method of claim 1, wherein 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is administered orally.

7. The method of claim 6, wherein the dose of 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is administered in an oral aqueous solution.

8. The method of claim 1, wherein 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is administered orally at a dose of 0.25 mg/kg for a subject with a body weight of less than 20 kg.

9. The method of claim 1, wherein 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is administered orally at a dose of 5 mg for a subject with a body weight of more than or equal to 20 kg.

10. The method of claim 1, wherein 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is administered once a day.

11. The method of claim 10, wherein 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is administered orally at a dose of 0.25 mg/kg per day for a subject with a body weight of less than 20 kg.

12. The method of claim 10, wherein 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is administered orally at a dose of 5 mg per day for a subject with a body weight of more than or equal to 20 kg.

13. A method of treating spinal muscular atrophy (SMA) in a subject in need thereof comprising administering to said subject a pharmaceutical composition comprising 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof, wherein the administered dose of 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is
   a. 0.25 mg/kg for a subject with a body weight of less than 20 kg, and
   b. 5 mg for a subject with a body weight of more than or equal to 20 kg.

14. The method of claim 13, wherein the SMA is type II SMA.

15. The method of claim 13, wherein the SMA is type III SMA.

16. The method of claim 13, wherein the SMA is type II SMA and type III SMA.

17. The method of claim 13, wherein the subject is more than or equal to 2 years of age.

18. The method of claim 13, wherein the dose of 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is administered in a single pharmaceutical composition.

19. The method of claim 13, wherein the dose of 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is administered in more than one pharmaceutical composition.

20. The method of claim 13, wherein the pharmaceutical composition is administered orally.

21. The method of claim 20, wherein the pharmaceutical composition is an oral aqueous solution.

22. The method of claim 13, wherein the pharmaceutical composition to administer 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof at a dose of 0.25 mg/kg for a subject with a body weight of less than 20 kg is a pharmaceutical composition for oral administration.

23. The method of claim 13, wherein the pharmaceutical composition to administer 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof at a dose of 5 mg for a subject with a body weight of more than or equal to 20 kg is a pharmaceutical composition for oral administration.

24. The method of claim 13, wherein the pharmaceutical composition to administer 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is administered once a day.

25. The method of claim 13, wherein the pharmaceutical composition to administer 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof at a dose of 0.25 mg/kg for a subject with a body weight of less than 20 kg is a pharmaceutical composition for administration once a day.

26. The method of claim 25, wherein the pharmaceutical composition to administer 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof at a dose of 0.25 mg/kg for a subject with a body weight of less than 20 kg is a pharmaceutical composition for oral administration.

27. The method of claim 13, wherein the pharmaceutical composition to administer 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof at a dose of 5 mg for a subject with a body weight of more than or equal to 20 kg is a pharmaceutical composition for administration once a day.

28. The method of claim 27, wherein the pharmaceutical composition to administer 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof at a dose of 5 mg for a subject with a body weight of more than or equal to 20 kg is a pharmaceutical composition for oral administration.

29. The method of claim 20, wherein the pharmaceutical composition is in powder form suitable for constitution of an oral solution.

30. A method of treating spinal muscular atrophy (SMA) in a subject in need thereof comprising administering to said subject 7-(4,7-diazaspiro[2.5]octan-7-yl)-2-(2,8-dimethylimidazo[1,2-b]pyridazin-6-yl)pyrido[1,2-a]pyrimidin-4-one, or a pharmaceutically acceptable salt thereof, wherein the administered daily dose of 7-(4,7-diazaspiro[2.5]octan-7-yl)-2-(2,8-dimethylimidazo[1,2-b]pyridazin-6-yl)pyrido[1,2-a]pyrimidin-4-one, or a pharmaceutically acceptable salt thereof, is 0.25 mg/kg for a subject 2 years of age and older with a body weight of less than 20 kg, and wherein the 7-(4,7-diazaspiro[2.5]octan-7-yl)-2-(2,8-dimethylimidazo[1,2-b]pyridazin-6-yl)pyrido[1,2-a]pyrimidin-4-one, or a pharmaceutically acceptable salt thereof, is administered in an oral solution constituted from a powder form of the 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof.

31. A method of treating spinal muscular atrophy (SMA) in a subject in need thereof comprising administering to said subject 7-(4,7-diazaspiro[2.5]octan-7-yl)-2-(2,8-dimethylimidazo[1,2-b]pyridazin-6-yl)pyrido[1,2-a]pyrimidin-4-one, or a pharmaceutically acceptable salt thereof, wherein the administered daily dose of 7-(4,7-diazaspiro[2.5]octan-7-yl)-2-(2,8-dimethylimidazo[1,2-b]pyridazin-6-yl)pyrido[1,2-a]pyrimidin-4-one, or a pharmaceutically acceptable salt thereof, is 5 mg for a subject 2 years of age and older with a body weight of more than or equal to 20 kg, and wherein the 7-(4,7-diazaspiro[2.5]octan-7-yl)-2-(2,8-dimethylimidazo[1,2-b]pyridazin-6-yl)pyrido[1,2-a]pyrimidin-4-one, or a pharmaceutically acceptable salt thereof, is administered in an oral solution constituted from a powder form of the 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof.

32. A method of treating spinal muscular atrophy (SMA) in a subject in need thereof comprising administering to said subject 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof, wherein the administered dose of 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof is a. 0.15 mg/kg to 0.25 mg/kg for a subject with a body weight of less than 20 kg, and b. 5 mg for a subject with a body weight of more than or equal to 20 kg.

33. The method of claim 32, wherein the 7-(4,7-diazaspiro[2.5]octan-7-yl)-2-(2,8-dimethylimidazo[1,2-b]pyridazin-6-yl)pyrido[1,2-a]pyrimidin-4-one, or a pharmaceutically acceptable salt thereof, is administered orally.

34. The method of claim 33, wherein the 7-(4,7-diazaspiro[2.5]octan-7-yl)-2-(2,8-dimethylimidazo[1,2-b]pyridazin-6-yl)pyrido[1,2-a]pyrimidin-4-one, or a pharmaceutically acceptable salt thereof, is administered as an oral solution.

35. The method of claim 32, wherein the 7-(4,7-diazaspiro[2.5]octan-7-yl)-2-(2,8-dimethylimidazo[1,2-b]pyridazin-6-yl)pyrido[1,2-a]pyrimidin-4-one, or a pharmaceutically acceptable salt thereof, is administered daily.

* * * * *